United States Patent
Marraffini et al.

(10) Patent No.: US 11,453,874 B2
(45) Date of Patent: Sep. 27, 2022

(54) ENHANCEMENT OF CRISPR GENE EDITING OR TARGET DESTRUCTION BY CO-EXPRESSION OF HETEROLOGOUS DNA REPAIR PROTEIN

(71) Applicant: The Rockefeller University, New York, NY (US)

(72) Inventors: Luciano Marraffini, Brooklyn, NY (US); Jon McGinn, New York, NY (US); Josh Modell, New York, NY (US); Dominik Paquet, Munich (DE)

(73) Assignee: The Rockefeller University, New York, NY (US)

( * ) Notice: Subject to any disclaimer, the term of this patent is extended or adjusted under 35 U.S.C. 154(b) by 468 days.

(21) Appl. No.: 16/620,366

(22) PCT Filed: Jun. 6, 2018

(86) PCT No.: PCT/US2018/036289
§ 371 (c)(1),
(2) Date: Dec. 6, 2019

(87) PCT Pub. No.: WO2018/226853
PCT Pub. Date: Dec. 13, 2018

(65) Prior Publication Data
US 2020/0140847 A1    May 7, 2020

Related U.S. Application Data

(60) Provisional application No. 62/516,634, filed on Jun. 7, 2017.

(51) Int. Cl.
| | | |
|---|---|---|
| *C12N 15/10* | (2006.01) | |
| *C12N 9/22* | (2006.01) | |
| *C12N 15/11* | (2006.01) | |
| *C12N 15/90* | (2006.01) | |
| *C12P 19/34* | (2006.01) | |
| *C12N 9/16* | (2006.01) | |
| *C12N 15/09* | (2006.01) | |

(52) U.S. Cl.
CPC ............ *C12N 15/102* (2013.01); *C12N 9/22* (2013.01); *C12N 15/111* (2013.01); *C12N 15/90* (2013.01); *C12P 19/34* (2013.01); *C12N 2310/20* (2017.05); *C12Y 301/11005* (2013.01); *C12Y 306/04012* (2013.01)

(58) Field of Classification Search
None
See application file for complete search history.

(56) References Cited

U.S. PATENT DOCUMENTS

2017/0114334 A1    4/2017    May et al.
2018/0346905 A1*  12/2018    McBrine ............... C12N 15/86

FOREIGN PATENT DOCUMENTS

| WO | 2016/099887 A1 | 6/2016 |
| WO | 2016094874 A1 | 6/2016 |
| WO | 2017009399 A1 | 1/2017 |

OTHER PUBLICATIONS

Wigley, D. B., Bacterial DNA repair: recent insights into the mechanism of RecBCD, AddAB and AdnAB, Nature Reviews Microbiology, Jan. 2013, vol. 11, No. 1, pp. 9-13.
McGinn, J. et al., Molecular mechanisms of CRISPR-Cas spacer acquisition, Nature Reviews Microbiology, Aug. 31, 2018, vol. 17, No. 1, pp. 7-12.
Zuniga-Castillo, J., et al., The Recombination Genes addAB Are Not Restricted to Gram-Positive Bacteria: Genetic Analysis of the Recombination Initiation Enzymes RecF and AddAB in Rhizobium etli, Journal of Bacteriology, Dec. 2004, vol. 186, No. 23, pp. 7905-7913.
Selle, K., et al., Harnessing CRISPR-Cas systems for bacterial genome editing, Trends in Microbiology, Feb. 17, 2015, vol. 23, No. 4, pp. 225-232.
Dillingham, M.S., et al., RecBCD Enzyme and the Repair of Double-Stranded DNA Breaks, Microbiology and Molecular Biology Reviews, Dec. 2008, vol. 72, No. 4, pp. 642-671.
Zhang, L., et al., The adnAB Locus, Encoding a Putative Helicase-Nuclease Activity, Is Essential in Streptomyces, Journal of Bacteriology, May 16, 2014, vol. 196, No. 14, pp. 2701-2708.

* cited by examiner

*Primary Examiner* — Suzanne M Noakes
*Assistant Examiner* — Jae W Lee
(74) *Attorney, Agent, or Firm* — Hodgson Russ LLP

(57) ABSTRACT

Provided are compositions, methods, and kits for improving CRISPR-based editing of DNA targets by a CRISPR-associated (Cas) enzyme. The improvement is made by combining the Cas enzyme and a CRISPR targeting RNA a heterologous DNA repair enzyme that is at least one of RecBCD, AddAB, or AdnAB. The heterologous DNA repair enzyme may have inactivated nuclease activity. The method can include using a DNA repair template to introduce one or more changes into the edited DNA. Cells that contain components of the improved CRISPR systems are included, as are kits for making such cells.

8 Claims, 4 Drawing Sheets

Specification includes a Sequence Listing.

SEQUENCE LISTING

```
<160> NUMBER OF SEQ ID NOS: 11

<210> SEQ ID NO 1
<211> LENGTH: 2279
<212> TYPE: DNA
<213> ORGANISM: artificial sequence
<220> FEATURE:
<223> OTHER INFORMATION: MLM3636_APP-gRNA plasmid sequence

<400> SEQUENCE: 1
gacgtcgcta gctgtacaaa aaagcaggct ttaaaggaac caattcagtc gactggatcc      60
ggtaccaagg tcgggcagga agagggccta tttcccatga ttccttcata tttgcatata     120
cgatacaagg ctgttagaga gataattaga attaatttga ctgtaaacac aaagatatta     180
gtacaaaata cgtgacgtag aaagtaataa tttcttgggt agtttgcagt tttaaaatta     240
tgttttaaaa tggactatca tatgcttacc gtaacttgaa agtatttcga tttcttggct     300
ttatatatct tgtggaaagg acgaaacacc ggagatctct gaagtgaaga gttttagagc     360
tagaaatagc aagttaaaat aaggctagtc cgttatcaac ttgaaaaagt ggcaccgagt     420
cggtgctttt tttaagcttg gccgctcga ggtacctctc tacatatgac atgtgagcaa     480
aaggccagca aaaggccagg aaccgtaaaa aggccgcgtt gctggcgttt ttccataggc     540 tccgccccc tgacgagcat cacaaaaatc gacgctcaag tcagaggtgg cgaaacccga     600
caggactata aagataccag gcgtttcccc ctggaagctc cctcgtgcgc tctcctgttc     660
cgaccctgcc gcttaccgga tacctgtccg cctttctccc ttcgggaagc gtggcgcttt     720
ctcatagctc acgctgtagg tatctcagtt cggtgtaggt cgttcgctcc aagctgggct     780
gtgtgcacga accccccgtt cagcccgacc gctgcgcctt atccggtaac tatcgtcttg     840
agtccaaccc ggtaagacac gacttatcgc cactggcagc agccactggt aacaggatta     900
gcagagcgag gtatgtaggc ggtgctacag agttcttgaa gtggtggcct aactacggct     960
acactagaag aacagtattt ggtatctgcg ctctgctgaa gccagttacc ttcggaaaaa    1020
```

-continued

```
gagttggtag ctcttgatcc ggcaaacaaa ccaccgctgg tagcggtggt ttttttgttt    1080
gcaagcagca gattacgcgc agaaaaaaag gatctcaaga agatcctttg atcttttcta    1140
cggggtctga cgctcagtgg aacgaaaact cacgttaagg gattttggtc atgagattat    1200
caaaaaggat cttcacctag atccttttaa attaaaaatg aagttttaaa tcaatctaaa    1260
gtatatatga gtaaacttgg tctgacagtt accaatgctt aatcagtgag gcacctatct    1320
cagcgatctg tctatttcgt tcatccatag ttgcctgact ccccgtcgtg tagataacta    1380
cgatacggga gggcttacca tctggcccca gtgctgcaat gataccgcga gacccacgct    1440
caccggctcc agatttatca gcaataaacc agccagccgg aagggccgag cgcagaagtg    1500
gtcctgcaac tttatccgcc tccatccagt ctattaattg ttgccgggaa gctagagtaa    1560
gtagttcgcc agttaatagt ttgcgcaacg ttgttgccat tgctacaggc atcgtggtgt    1620
cacgctcgtc gtttggtatg gcttcattca gctccggttc ccaacgatca aggcgagtta    1680
catgatcccc catgttgtgc aaaaaagcgg ttagctcctt cggtcctccg atcgttgtca    1740
gaagtaagtt ggccgcagtg ttatcactca tggttatggc agcactgcat aattctctta    1800
ctgtcatgcc atccgtaaga tgcttttctg tgactggtga gtactcaacc aagtcattct    1860
gagaatagtg tatgcggcga ccgagttgct cttgcccggc gtcaatacgg gataataccg    1920
cgccacatag cagaacttta aaagtgctca tcattggaaa acgttcttcg ggcgaaaac    1980 tctcaaggat cttaccgctg ttgagatcca gttcgatgta acccactcgt gcacccaact    2040
gatcttcagc atcttttact ttcaccagcg tttctgggtg agcaaaaaca ggaaggcaaa    2100
atgccgcaaa aagggaata agggcgacac ggaaatgttg aatactcata ctcttccttt    2160
ttcaatatta ttgaagcatt tatcagggtt attgtctcat gagcggatac atatttgaat    2220
gtatttagaa aaataaacaa ataggggttc cgcgcacatt tccccgaaaa gtgccacct    2279
```

<210> SEQ ID NO 2
<211> LENGTH: 2278
<212> TYPE: DNA
<213> ORGANISM: artificial sequence
<220> FEATURE:
<223> OTHER INFORMATION: MLM3636_PSEN1-gR plasmid

<400> SEQUENCE: 2

```
gacgtcgcta gctgtacaaa aaagcaggct ttaaaggaac caattcagtc gactggatcc      60
ggtaccaagg tcgggcagga agagggccta tttcccatga ttccttcata tttgcatata     120
cgatacaagg ctgttagaga gataattaga attaatttga ctgtaaacac aaagatatta     180
gtacaaaata cgtgacgtag aaagtaataa tttcttgggt agtttgcagt tttaaaatta     240
tgttttaaaa tggactatca tatgcttacc gtaacttgaa agtatttcga tttcttggct     300
ttatatatct tgtggaaagg acgaaacacc gttgtcgtga ctatcctccg ttttagagct     360
agaaatagca agttaaaata aggctagtcc gttatcaact tgaaaaagtg gcaccgagtc     420
ggtgcttttt ttaagcttgg gccgctcgag gtacctctct acatatgaca tgtgagcaaa     480
aggccagcaa aaggccagga accgtaaaaa ggccgcgttg ctggcgtttt tccataggct     540
ccgcccccct gacgagcatc acaaaaatcg acgctcaagt cagaggtggc gaaacccgac     600
aggactataa agataccagg cgtttccccc tggaagctcc ctcgtgcgct ctcctgttcc     660
gaccctgccg cttaccggat acctgtccgc ctttctccct tcgggaagcg tggcgctttc     720
tcatagctca cgctgtaggt atctcagttc ggtgtaggtc gttcgctcca agctgggctg     780
tgtgcacgaa ccccccgttc agcccgaccg ctgcgcctta tccggtaact atcgtcttga     840
```

```
gtccaacccg gtaagacacg acttatcgcc actggcagca gccactggta acaggattag      900
cagagcgagg tatgtaggcg gtgctacaga gttcttgaag tggtggccta actacggcta      960
cactagaaga acagtatttg gtatctgcgc tctgctgaag ccagttacct tcggaaaaag     1020
agttggtagc tcttgatccg gcaaacaaac caccgctggt agcggtggtt ttttttgtttg    1080 caagcagcag attacgcgca gaaaaaaagg atctcaagaa gatcctttga tcttttctac    1140
ggggtctgac gctcagtgga acgaaaactc acgttaaggg attttggtca tgagattatc    1200
aaaaaggatc ttcacctaga tccttttaaa ttaaaaatga agttttaaat caatctaaag    1260
tatatatgag taaacttggt ctgacagtta ccaatgctta atcagtgagg cacctatctc    1320
agcgatctgt ctatttcgtt catccatagt tgcctgactc ccgtcgtgt agataactac      1380 gatacgggag ggcttaccat ctggccccag tgctgcaatg ataccgcgag acccacgctc    1440
accggctcca gatttatcag caataaacca gccagccgga agggccgagc gcagaagtgg    1500
tcctgcaact ttatccgcct ccatccagtc tattaattgt tgccgggaag ctagagtaag    1560
tagttcgcca gttaatagtt tgcgcaacgt tgttgccatt gctacaggca tcgtggtgtc    1620
acgctcgtcg tttggtatgg cttcattcag ctccggttcc caacgatcaa ggcgagttac    1680
atgatccccc atgttgtgca aaaaagcggt tagctccttc ggtcctccga tcgttgtcag    1740
aagtaagttg gccgcagtgt tatcactcat ggttatggca gcactgcata attctcttac    1800
tgtcatgcca tccgtaagat gcttttctgt gactggtgag tactcaacca agtcattctg    1860
agaatagtgt atgcggcgac cgagttgctc ttgcccggcg tcaatacggg ataataccgc    1920
gccacatagc agaactttaa aagtgctcat cattggaaaa cgttcttcgg ggcgaaaact    1980
ctcaaggatc ttaccgctgt tgagatccag ttcgatgtaa cccactcgtg cacccaactg    2040
atcttcagca tcttttactt tcaccagcgt ttctgggtga gcaaaaacag gaaggcaaaa    2100
tgccgcaaaa aagggaataa gggcgacacg gaaatgttga atactcatac tcttcctttt    2160
tcaatattat tgaagcattt atcagggtta ttgtctcatg agcggataca tatttgaatg    2220
tatttagaaa aataaacaaa tagggggttcc gcgcacattt ccccgaaaag tgccacct     2278
```

<210> SEQ ID NO 3
<211> LENGTH: 9271
<212> TYPE: DNA
<213> ORGANISM: artificial sequence
<220> FEATURE:
<223> OTHER INFORMATION: pCas9_2A_GFP plasmid

<400> SEQUENCE: 3

```
actagttatt aatagtaatc aattacgggg tcattagttc atagcccata tatggagttc      60
cgcgttacat aacttacggt aaatggcccg cctggctgac cgcccaacga cccccgccca    120
ttgacgtcaa taatgacgta tgttcccata gtaacgccaa tagggacttt ccattgacgt    180
caatgggtgg actatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtgt cgaggtgagcc ccacgttctg cttcactctc cccatctccc ccccctcccc    420
acccccaatt ttgtatttat ttattttttta attattttgt gcagcgatgg gggcgggggg    480
ggggggggcg cgcgccaggc ggggcgggggc ggggcgaggg gcgggggcggg gcgaggcgga    540 gaggtgcggc ggcagccaat cagagcggcg cgctccgaaa gtttcctttt atggcgaggc    600
```

-continued

```
ggcggcggcg gcggccctat aaaaagcgaa gcgcgcggcg ggcgggagtc gctgcgttgc         660
cttcgccccg tgccccgctc cgcgccgcct cgcgccgccc gccccggctc tgactgaccg         720
cgttactccc acaggtgagc gggcgggacg gcccttctcc tccgggctgt aattagcgct         780
tggtttaatg acggctcgtt tcttttctgt ggctgcgtga aagccttaaa gggctccggg         840
agggcccttt gtgcgggggg gagcggctcg ggggtgcgt gcgtgtgtgt gtgcgtgggg         900
agcgccgcgt gcgcccgcg ctgcccgcg gctgtgagcg ctgcgggcgc ggcgcggggc         960
tttgtgcgct ccgcgtgtgc gcgaggggag cgcggccggg ggcggtgccc cgcggtgcgg        1020
gggggctgcg aggggaacaa aggctgcgtg cggggtgtgt gcgtgggggg gtgagcaggg        1080
ggtgtgggcg cggcggtcgg gctgtaaccc ccccctgcac cccccctcccc gagttgctga        1140 gcacggcccg gcttcgggtg cggggctccg tacggggcgt ggcgcggggc tcgccgtgcc        1200 gggcggggg tggcggcagg tggggtgcc gggcggggcg gggccgcctc gggccgggga        1260
gggctcgggg gaggggcgcg gcggcccccg gagcgccggc ggctgtcgag gcgcggcgag        1320
ccgcagccat tgccttttat ggtaatcgtg cgagagggcg cagggacttc ctttgtccca        1380
aatctgtgcg gagccgaaat ctggaggcg ccgccgcacc ccctctagcg ggcgcggggc        1440
gaagcggtgc ggcgccggca ggaaggaaat gggcgggag ggccttcgtg cgtcgccgcg        1500
ccgccgtccc cttctccatc tccagcctcg ggctgtccg caggggacg gctgccttcg        1560 gggggggacgg ggcagggcgg ggttcggctt ctggcgtgtg accggcggct ctagtgcctc        1620
tgctaaccat gttcatgcct tcttcttttt cctacagctc ctgggcaacg tgctggttat        1680
tgtgctgtct catcattttg gcaaagaatt cgcggccgcc accatggaca agaagtactc        1740
cattgggctc gatatcggca caaacagcgt cggctgggcc gtcattacgg acgagtacaa        1800
ggtgccgagc aaaaaattca agttctggg caataccgat cgccacagca taagaagaa        1860 cctcattggc gccctcctgt tcgactccgg ggagacggcc gaagccacgc ggctcaaaag        1920
aacagcacgg cgcagatata cccgcagaaa gaatcggatc tgctacctgc aggagatctt        1980
tagtaatgag atggctaagg tggatgactc tttcttccat aggctggagg agtccttttt        2040
ggtggaggag gataaaaagc acgagcgcca cccaatcttt ggcaatatcg tggacgaggt        2100
ggcgtaccat gaaaagtacc caaccatata tcatctgagg aagaagcttg tagacagtac        2160
tgataaggct gacttgcggt tgatctatct cgcgctggcg catatgatca aatttcgggg        2220
acacttcctc atcgaggggg acctgaaccc agacaacagc gatgtcgaca aactctttat        2280
ccaactggtt cagacttaca atcagctttt cgaagagaac ccgatcaacg catccggagt        2340
tgacgccaaa gcaatcctga gcgctaggct gtccaaatcc cggcggctcg aaaacctcat        2400
cgcacagctc cctggggaga agaagaacgg cctgtttggt aatcttatcg ccctgtcact        2460
cgggctgacc cccaacttta atctaacttt cgacctggcc gaagatgcca agcttcaact        2520
gagcaaagac acctacgatg atgatctcga caatctgctg gcccagatcg gcgaccagta        2580
cgcagacctt tttttggcgg caaagaacct gtcagacgcc attctgctga gtgatattct        2640
gcgagtgaac acggagatca ccaaagctcc gctgagcgct agtatgatca agcgctatga        2700
tgagcaccac caagacttga ctttgctgaa ggcccttgtc agacagcaac tgcctgagaa        2760
gtacaaggaa attttcttcg atcagtctaa aaatggctac gccggataca ttgacggcgg        2820
agcaagccag gaggaatttt acaaatttat taagcccatc ttggaaaaaa tggacggcac        2880
cgaggagctg ctggtaaagc ttaacagaga agatctgttg cgcaaacagc gcactttcga        2940
caatggaagc atcccccacc agattcacct gggcgaactg cacgctatcc tcaggcggca        3000
```

```
agaggatttc tacccctttt tgaaagataa cagggaaaag attgagaaaa tcctcacatt    3060
tcggataccc tactatgtag gcccctcgc ccggggaaat tccagattcg cgtggatgac    3120
tcgcaaatca gaagagacca tcactccctg gaacttcgag gaagtcgtgg ataaggggc    3180
ctctgcccag tccttcatcg aaaggatgac taactttgat aaaaatctgc ctaacgaaaa    3240
ggtgcttcct aaacactctc tgctgtacga gtacttcaca gtttataacg agctcaccaa    3300
ggtcaaatac gtcacagaag ggatgagaaa gccagcattc ctgtctggag agcagaagaa    3360
agctatcgtg gacctcctct tcaagacgaa ccggaaagtt accgtgaaac agctcaaaga    3420
agactatttc aaaaagattg aatgtttcga ctctgttgaa atcagcggag tggaggatcg    3480
cttcaacgca tccctgggaa cgtatcacga tctcctgaaa atcattaaag acaaggactt    3540
cctggacaat gaggagaacg aggacattct tgaggacatt gtcctcaccc ttacgttgtt    3600
tgaagatagg gagatgattg aagaacgctt gaaaacttac gctcatctct tcgacgacaa    3660
agtcatgaaa cagctcaaga ggcgccgata tacaggatgg gggcggctgt caagaaaact    3720
gatcaatggg atccgagaca agcagagtgg aaagacaatc ctggattttc ttaagtccga    3780
tggatttgcc aaccggaact tcatgcagtt gatccatgat gactctctca cctttaagga    3840
ggacatccag aaagcacaag tttctggcca gggggacagt cttcacgagc acatcgctaa    3900
tcttgcaggt agcccagcta tcaaaaaggg aatactgcag accgttaagg tcgtggatga    3960
actcgtcaaa gtaatgggaa ggcataagcc cgagaatatc gttatcgaga tggcccgaga    4020
gaaccaaact acccagaagg gacagaagaa cagtagggaa aggatgaaga ggattgaaga    4080
gggtataaaa gaactggggt cccaaatcct taaggaacac ccagttgaaa acacccagct    4140
tcagaatgag aagctctacc tgtactacct gcagaacggc agggacatgt acgtggatca    4200
ggaactggac atcaatcggc tctccgacta cgacgtggat catatcgtgc cccagtctt    4260
tctcaaagat gattctattg ataataaagt gttgacaaga tccgataaaa atagagggaa    4320
gagtgataac gtcccctcag aagaagttgt caagaaaatg aaaaattatt ggcggcagct    4380
gctgaacgcc aaactgatca cacaacggaa gttcgataat ctgactaagg ctgaacgagg    4440
tggcctgtct gagttggata agccggcttc atcaaaagg cagcttgttg agacacgcca    4500
gatcaccaag cacgtggccc aaattctcga ttcacgcatg aacaccaagt acgatgaaaa    4560
tgacaaactg attcgagagg tgaaagttat tactctgaag tctaagctgg tctcagattt    4620
cagaaaggac tttcagtttt ataaggtgag agagatcaac aattaccacc atgcgcatga    4680
tgcctacctg aatgcagtgg taggcactgc acttatcaaa aaatatccca agcttgaatc    4740
tgaatttgtt tacggagact ataaagtgta cgatgttagg aaaatgatcg caaagtctga    4800
gcaggaaata ggcaaggcca ccgctaagta cttcttttac agcaatatta tgaatttttt    4860
caagaccgag attacactgg ccaatggaga gattcggaag cgaccactta tcgaaacaaa    4920
cggagaaaca ggagaaatcg tgtgggacaa gggtagggat ttcgcgacag tccggaaggt    4980
cctgtccatg ccgcaggtga acatcgttaa aaagaccgaa gtacagaccg gaggcttctc    5040
caaggaaagt atcctcccga aaaggaacag cgacaagctg atcgcacgca aaaaagattg    5100
ggaccccaag aaatacggcg gattcgattc tcctacagtc gcttacagtg tactggttgt    5160
ggccaaagtg gagaaaggga gtctaaaaaa actcaaaagc gtcaaggaac tgctgggcat    5220
cacaatcatg gagcgatcaa gcttcgaaaa aaacccatc gactttctcg aggcgaaagg    5280
atataaagag gtcaaaaaag acctcatcat taagcttccc aagtactctc tctttgagct    5340
```

```
tgaaaacggc cggaaacgaa tgctcgctag tgcgggcgag ctgcagaaag gtaacgagct    5400
ggcactgccc tctaaatacg ttaatttctt gtatctggcc agccactatg aaaagctcaa    5460
agggtctccc gaagataatg agcagaagca gctgttcgtg aacaacaca  aacactacct    5520 tgatgagatc atcgagcaaa taagcgaatt ctccaaaaga gtgatcctcg ccgacgctaa    5580
cctcgataag gtgctttctg cttacaataa gcacagggat aagcccatca gggagcaggc    5640
agaaaacatt atccacttgt ttactctgac caacttgggc gcgcctgcag ccttcaagta    5700
cttcgacacc accatagaca gaaagcggta cacctctaca aaggaggtcc tggacgccac    5760
actgattcat cagtcaatta cggggctcta tgaaacaaga atcgacctct ctcagctcgg    5820
tggagacagc agggctgacc ccaagaagaa gaggaaggtg aggtccggcg gcggagaggg    5880
cagaggaagt cttctaacat gcggtgacgt ggaggagaat cccggcccaa tggtgagcaa    5940
gggcgaggag ctgttcaccg gggtggtgcc catcctggtc gagctggacg gcgacgtaaa    6000
cggccacaag ttcagcgtgt ccggcgaggg cgagggcgat gccacctacg gcaagctgac    6060
cctgaagttc atctgcacca ccggcaagct gcccgtgccc tggcccaccc tcgtgaccac    6120
cctgacctac ggcgtgcagt gcttcagccg ctaccccgac cacatgaagc agcacgactt    6180
cttcaagtcc gccatgcccg aaggctacgt ccaggagcgc accatcttct tcaaggacga    6240
cggcaactac aagacccgcg ccgaggtgaa gttcgagggc gacaccctgg tgaaccgcat    6300
cgagctgaag ggcatcgact tcaaggagga cggcaacatc ctggggcaca gctggagta   6360 caactacaac agccacaacg tctatatcat ggccgacaag cagaagaacg gcatcaaggt    6420
gaacttcaag atccgccaca acatcgagga cggcagcgtg cagctcgccg accactacca    6480
gcagaacacc cccatcggcg acggccccgt gctgctgccc gacaaccact acctgagcac    6540
ccagtccgcc ctgagcaaag accccaacga gaagcgcgat cacatggtcc tgctggagtt    6600
cgtgaccgcc gccgggatca ctctcggcat ggacgagctg tacaagtaac tgcagcgcgg    6660
ggatctcatg ctggagttct tcgcccaccc caacttgttt attgcagctt ataatggtta    6720
caaataaagc aatagcatca caaatttcac aaataaagca ttttttttcac tgcattctag    6780 ttgtggtttg tccaaactca tcaatgtatc ttatcatgtc tgtataccgt cgacctctag    6840
ctagagcttg gcgtaatcat ggtcatagct gtttcctgtg tgaaattgtt atccgctcac    6900
aattccacac aacatacgag ccggaagcat aaagtgtaaa gcctagggtg cctaatgagt    6960
gagctaactc acattaattg cgttgcgctc actgcccgct ttccagtcgg gaaacctgtc    7020
gtgccagctg cattaatgaa tcggccaacg cgcgggggaga ggcggtttgc gtattgggcg    7080
ctcttccgct tcctcgctca ctgactcgct gcgctcggtc gttcggctgc ggcgagcggt    7140
atcagctcac tcaaaggcgg taatacggtt atccacagaa tcaggggata acgcaggaaa    7200
gaacatgtga gcaaaaggcc agcaaaaggc caggaaccgt aaaaaggccg cgttgctggc    7260
gtttttccat aggctccgcc cccctgacga gcatcacaaa aatcgacgct caagtcagag    7320
gtggcgaaac ccgacaggac tataaagata ccaggcgttt ccccctggaa gctccctcgt    7380
gcgctctcct gttccgaccc tgccgcttac cggatacctg tccgcctttc tcccttcggg    7440
aagcgtggcg ctttctcata gctcacgctg taggtatctc agttcggtgt aggtcgttcg    7500
ctccaagctg ggctgtgtgc acgaaccccc cgttcagccc gaccgctgcg ccttatccgg    7560
taactatcgt cttgagtcca acccggtaag acacgactta tcgccactgg cagcagccac    7620
tggtaacagg attagcagag cgaggtatgt aggcggtgct acagagttct tgaagtggtg    7680
gcctaactac ggctacacta gaagaacagt atttggtatc tgcgctctgc tgaagccagt    7740
```

| | |
|---|---|
| taccttcgga aaaagagttg gtagctcttg atccggcaaa caaaccaccg ctggtagcgg | 7800 |
| tggttttttt gtttgcaagc agcagattac gcgcagaaaa aaaggatctc aagaagatcc | 7860 |
| tttgatcttt tctacggggt ctgacgctca gtggaacgaa aactcacgtt aagggatttt | 7920 |
| ggtcatgaga ttatcaaaaa ggatcttcac ctagatcctt ttaaattaaa aatgaagttt | 7980 |
| taaatcaatc taaagtatat atgagtaaac ttggtctgac agttaccaat gcttaatcag | 8040 |
| tgaggcacct atctcagcga tctgtctatt tcgttcatcc atagttgcct gactccccgt | 8100 |
| cgtgtagata actacgatac gggagggctt accatctggc cccagtgctg caatgatacc | 8160 |
| gcgagaccca cgctcaccgg ctccagattt atcagcaata aaccagccag ccggaagggc | 8220 |
| cgagcgcaga agtggtcctg caactttatc cgcctccatc cagtctatta attgttgccg | 8280 |
| ggaagctaga gtaagtagtt cgccagttaa tagtttgcgc aacgttgttg ccattgctac | 8340 |
| aggcatcgtg gtgtcacgct cgtcgtttgg tatggcttca ttcagctccg gttcccaacg | 8400 |
| atcaaggcga gttacatgat cccccatgtt gtgcaaaaaa gcggttagct ccttcggtcc | 8460 |
| tccgatcgtt gtcagaagta agttggccgc agtgttatca ctcatggtta tggcagcact | 8520 |
| gcataattct cttactgtca tgccatccgt aagatgcttt tctgtgactg gtgagtactc | 8580 |
| aaccaagtca ttctgagaat agtgtatgcg gcgaccgagt tgctcttgcc cggcgtcaat | 8640 |
| acgggataat accgcgccac atagcagaac tttaaaagtg ctcatcattg gaaaacgttc | 8700 |
| ttcggggcga aaactctcaa ggatcttacc gctgttgaga tccagttcga tgtaacccac | 8760 |
| tcgtgcaccc aactgatctt cagcatcttt tactttcacc agcgtttctg gtgagcaaa | 8820 |
| aacaggaagg caaaatgccg caaaaaaggg aataagggcg acacggaaat gttgaatact | 8880 |
| catactcttc ctttttcaat attattgaag catttatcag ggttattgtc tcatgagcgg | 8940 |
| atacatattt gaatgtattt agaaaaataa acaaataggg gttccgcgca catttccccg | 9000 |
| aaaagtgcca cctgacgtcg acggatcggg agatcgatct cccgatcccc tagggtcgac | 9060 |
| tctcagtaca atctgctctg atgccgcata gttaagccag tatctgctcc ctgcttgtgt | 9120 |
| gttggaggtc gctgagtagt gcgcgagcaa aatttaagct acaacaaggc aaggcttgac | 9180 |
| cgacaattgc atgaagaatc tgcttagggt taggcgtttt gcgctgcttc gcgatgtacg | 9240 |
| ggccagatat acgcgttgac attgattatt g | 9271 |

<210> SEQ ID NO 4
<211> LENGTH: 8202
<212> TYPE: DNA
<213> ORGANISM: artificial sequence
<220> FEATURE:
<223> OTHER INFORMATION: pCS2+_EF1a_RexA_3xFLAG_NLS plasmid

<400> SEQUENCE: 4

| | |
|---|---|
| gtaattcata caaaaggact cgcccctgcc ttggggaatc ccagggaccg tcgttaaact | 60 |
| cccactaacg tagaacccag agatcgctgc gttcccgccc cctcacccgc ccgctctcgt | 120 |
| catcactgag gtggagaaga gcatgcgtga ggctccggtg cccgtcagtg gcagagcgc | 180 |
| acatcgccca cagtccccga gaagttgggg gaggggtcg gcaattgaac cggtgcctag | 240 |
| agaaggtggc gcggggtaaa ctgggaaagt gatgtcgtgt actggctccg ccttttttccc | 300 |
| gagggtgggg gagaaccgta tataagtgca gtagtcgccg tgaacgttct ttttcgcaac | 360 |
| gggtttgccg ccagaacaca ggtaagtgcc gtgtgtggtt cccgcgggcc tggcctcttt | 420 |
| acgggttatg gcccttgcgt gccttgaatt acttccacgc cctggctgc agtacgtgat | 480 |

```
tcttgatccc gagcttcggg ttggaagtgg gtgggagagt tcgaggcctt gcgcttaagg    540
agcccctttcg cctcgtgctt gagttgaggc ctggcttggg cgctggggcc gccgcgtgcg    600
aatctggtgg caccttcgcg cctgtctcgc tgctttcgat aagtctctag ccatttaaaa    660
tttttgatga cctgctgcga cgcttttttt ctggcaagat agtcttgtaa atgcgggcca    720
agatctgcac actggtattt cggttttttgg ggccgcgggc ggcgacgggg cccgtgcgtc    780
ccagcgcaca tgttcggcga ggcggggcct gcgagcgcgg ccaccgagaa tcggacgggg    840
gtagtctcaa gctggccggc ctgctctggt gcctggcctc gcgccgccgt gtatcgcccc    900
gccctgggcg gcaaggctgg cccggtcggc accagttgcg tgagcggaaa gatggccgct    960
tcccggccct gctgcaggga gctcaaaatg gaggacgcgg cgctcgggag agcgggcggg    1020
tgagtcaccc acacaaagga aaagggcctt ccgtcctca gccgtcgctt catgtgactc    1080
cacggagtac cgggcgccgt ccaggcacct cgattagttc tcgagctttt ggagtacgtc    1140
gtctttaggt tgggggggagg ggttttatgc gatggagttt ccccacactg agtgggtgga    1200
gactgaagtt aggccagctt ggcacttgat gtaattctcc ttggaatttg ccctttttga    1260
gtttggatct tggttcattc tcaagcctca gacagtggtt caaagttttt ttcttccatt    1320
tcaggtgtcg tgagactcgt ttagtgaacc gtcagatcgc ctggagacgc catccacgct    1380
gttttgacct ccatagaaga caccgggacc gatccagcct ccgcggcccc gaattcgcca    1440
ccatgatatc ttttgctcca ttcctgtccc ccgaggcaat caagcacctc caggaaaacg    1500
aaagatgtag ggatcagtcc caaaaagaa cggcacagca aatagaggct atctatacga    1560
gtggccagaa catacttgtt agcgcttctg caggagcgg gaagaccttc gtcatggttg    1620
agagaattct ggacaaaatc ttgagaggcg tatccataga tcggttgttc atttctactt    1680
tcaccgtgaa ggcagccact gagcttcgag agcgcattga aaataaattg tacagccaga    1740
ttgcgcaaac aactgacttt cagatgaagg tatatctgac cgagcaactt cagtctctgt    1800
gtcaagcgga cataggcacg atggatgcat tcgcccagaa agtggtttcc cgatatggct    1860
actccatcgg aatatcctca cagtttcgaa taatgcaaga taaagcagag caagacgttt    1920
tgaagcaaga agtctttttct aagcttttta atgagtttat gaatcaaaaa gaggccccag    1980
tctttcgagc gttggttaaa aatttctctg gaactgcaa agacacctct gcattcagag    2040
aattggtcta cacctgttat agctttagcc aatcaactga aaacccgaag atatggttgc    2100
aggaaaattt cctttccgca gcaaaaacgt accagaggct ggaagatatt ccagatcatg    2160
atattgaact cttgcttctt gcaatgcaag atacggcgaa ccaacttcgc gatgtcacgg    2220
acatggagga ctatggtcag ctcactaagg cagggagccg atcagcaaag tacactaagc    2280
accttacgat tatagagaag ctgagcgact gggttaggga ttttaaatgc ctctacggta    2340
aagctggtct ggacagattg atacgggacg ttacaggact gattcctagc ggtaacgatg    2400
ttaccgtgtc taaggtaaag taccctgtat tcaaaaacctt gcaccaaaag cttaagcaat    2460
ttaggcatct ggaaacgatc ctgatgtacc aaaaagactg tttctccctg ctcgaacagt    2520
tgcaagactt tgtattggcc ttttcagagg cttacttggc tgtgaagatt caggaatctg    2580
cgttcgaatt cagtgatatt gctcacttcg cgattaaaat cctggaggaa ataccgata    2640
ttcgccagag ctatcaacag cattatcacg aagtaatggt ggacgagtat caggataata    2700
accatatgca agaacgcctc ctcacactgc tctcaaacgg tcacaacaga tttatggtgg    2760
gtgatattaa gcagtcaatc tatcgattta gacaagccga cccgcaaatt tttaaccaga    2820
agtttcggga ttatcagaaa aagcccgagc agggaaaagt catcctcctg aaagagaatt    2880
```

```
tccgctccca gagtgaagtc cttaacgtct caaatgccgt ctttagccac cttatggacg    2940
aaagtgtcgg tgatgtactg tatgacgagc agcatcagtt gattgcagga agccatgccc    3000
aaaccgtccc gtacctcgac agacgcgcgc agctcctcct gtacaattcc gataaagatg    3060
acgggaatgc accgagcgac tctgaaggca taagcttctc tgaagttaca attgtcgcta    3120
aagagatcat caagctgcac aacgataagg gagtaccttt tgaagatatt actctgctcg    3180
tgtcttcccg gaccagaaac gatattatta gccatacatt taaccagtat ggaattccaa    3240
tagctacgga tgggggtcaa cagaattatc tgaaatccgt agaggtgatg gttatgctgg    3300
acacactcag aacgataaat aatccacgga acgactacgc actcgttgca ttgttgaggt    3360
ccccgatgtt tgcttcgac gaggacgact tggcgaggat cgctttgcaa aaagataatg    3420
agctggataa ggactgtctc tatgataaaa ttcagcgagc ggtaatcggc cggggtgcac    3480
accccgagtt gatacacgat accctgcttg ggaaacttaa tgttttcctc aagacattga    3540
aatcttggcg ccggtatgcg aagctcggct ctctctatga cctcatctgg aaaattttta    3600
atgaccgctt ttactttgac ttcgtggcaa gtcaagccaa ggcagaacag gcgcaggcca    3660
acctctatgc gctcgccctt cgggctaacc aatttgaaaa gtcagggtat aaggggttgt    3720
accgcttcat aaagatgatt gataaagtcc ttgaaactca gaatgacttg gcggacgtag    3780
aagtagcgac tccgaagcag gcagttaatc tgatgacaat tcataaaagt aaaggactgc    3840
aattcccata tgttttatc ttgaattgcg acaaacgatt tagtatgacg atatccaca     3900 agtcatttat actgaatagg caacatggta ttggtattaa gtacttggcc gatataaaag    3960
gcttgttggg ggaaacaaca cttaatagcg ttaaggtttc catggagaca ttgccatacc    4020
aactgaacaa gcaagagctc cgactcgcca cactgagtga ggaaatgaga ctcctgtatg    4080
tggcaatgac aagagctgag aagaaggtgt actttatcgg gaaggcctca aaaagtaaaa    4140
gccaagagat tactgatccc aaaaagctgg gtaaattgct tccccttgcg ttgagagagc    4200
agctgctcac atttcaagat tggcttcttg cgattgctga catattttcc actgaagatc    4260
tgtattttga cgtgaggttc attgaagact ccgacctcac tcaagaaagc gtgggtcgat    4320
tgcagactcc tcagctcctc aaccccgacg atctgaaaga caaccggcag tccgagacaa    4380
tagcacgggc attggatatg cttgaagcgg tttcccaact taatgccaat tatgaagcgg    4440
cgatacacct cccaaccgtc agaactccct cacaacttaa ggccacctat gagccgttgc    4500
tggaacccat cggtgtcgac ataattgaga atcatctag gtctctttcc gactttacac    4560
tcccccactt tagcaaaaag gctaaagtag aagcgtcaca cattggctca gccctccacc    4620
aactcatgca gtcctgccc ttgagtaagc caatcaacca gcagaccctc ctcgatgccc     4680
ttcgaggcat tgactcaaat gaggaagtca agacagcgtt ggatcttaaa aaattgagt     4740 ctttttttg cgacacatca ctcggccagt ttttccagac ataccaaaag catctgtata    4800
gagaagcgcc attcgctatt ttgaaactgg atccaataag tcaagaggag tatgtcctga    4860
gagggattat cgatgcgtac tttctgtttg atgatcatat tgtacttgta gactacaaaa    4920
cggacaaata taaacagcct atcgaactga aaaagcgcta ccaacaacag ttggaactgt    4980
acgcggaggc cctcacccaa acatataaac tccccgtcac aaagagatat ttggttctca    5040
tgggtggtgg caaacctgaa attgtagagg tcggctccgg agactataag gaccacgacg    5100
gagactacaa ggatcatgat attgattaca agacgatga cgataagggc tccggcaaaa     5160
ggccggcggc cacgaaaaag gccggccagg caaaaaagaa aaagtgaatc tagaactata    5220
```

```
gtgagtcgta ttacgtagat ccagacatga taagatacat tgatgagttt ggacaaacca    5280
caactagaat gcagtgaaaa aaatgcttta tttgtgaaat tgtgatgct attgctttat     5340 ttgtaaccat tataagctgc aataaacaag ttaacaacaa caattgcatt cattttatgt    5400
ttcaggttca gggggaggtg tgggaggttt tttaattcgc ggccgcggcg ccaatgcatt    5460
gggcccggta cccagctttt gttccctta gtgagggtta attgcgcgct tggcgtaatc     5520
atggtcatag ctgtttcctg tgtgaaattg ttatccgctc acaattccac acaacatacg    5580
agccggaagc ataaagtgta aagcctgggg tgcctaatga gtgagctaac tcacattaat    5640
tgcgttgcgc tcactgcccg ctttccagtc gggaaacctg tcgtgccagc tgcattaatg    5700
aatcggccaa cgcgcgggga gaggcggttt gcgtattggg cgctcttccg cttcctcgct    5760
cactgactcg ctgcgctcgg tcgttcggct gcggcgagcg gtatcagctc actcaaaggc    5820
ggtaatacgg ttatccacag aatcagggga taacgcagga agaacatgt gagcaaaagg      5880 ccagcaaaag gccaggaacc gtaaaaaggc cgcgttgctg gcgttttcc ataggctccg       5940 cccccctgac gagcatcaca aaaatcgacg ctcaagtcag aggtggcgaa acccgacagg     6000
actataaaga taccaggcgt ttccccctgg aagctccctc gtgcgctctc ctgttccgac     6060
cctgccgctt accggatacc tgtccgcctt ctcccttcg ggaagcgtgg cgctttctca      6120
tagctcacgc tgtaggtatc tcagttcggt gtaggtcgtt cgctccaagc tgggctgtgt     6180
gcacgaaccc cccgttcagc ccgaccgctg cgccttatcc ggtaactatc gtcttgagtc     6240
caacccggta agacacgact tatcgccact ggcagcagcc actggtaaca ggattagcag     6300
agcgaggtat gtaggcggtg ctacagagtt cttgaagtgg tggcctaact acggctacac     6360
tagaaggaca gtatttggta tctgcgctct gctgaagcca gttaccttcg gaaaaagagt     6420
tggtagctct tgatccggca acaaaccac cgctggtagc ggtggttttt tgtttgcaa      6480 gcagcagatt acgcgcagaa aaaaggatc tcaagaagat cctttgatct tttctacggg     6540
gtctgacgct cagtggaacg aaaactcacg ttaagggatt ttggtcatga gattatcaaa    6600
aaggatcttc acctagatcc ttttaaatta aaaatgaagt tttaaatcaa tctaaagtat    6660
atatgagtaa acttggtctg acagttacca atgcttaatc agtgaggcac ctatctcagc    6720
gatctgtcta tttcgttcat ccatagttgc ctgactcccc gtcgtgtaga taactacgat    6780
acgggagggc ttaccatctg gccccagtgc tgcaatgata ccgcgagacc cacgctcacc    6840
ggctccagat ttatcagcaa taaaccagcc agccggaagg gccgagcgca gaagtggtcc    6900
tgcaacttta tccgcctcca tccagtctat taattgttgc cgggaagcta gagtaagtag    6960
ttcgccagtt aatagtttgc gcaacgttgt tgccattgct acaggcatcg tggtgtcacg    7020
ctcgtcgttt ggtatggctt cattcagctc cggttcccaa cgatcaaggc gagttacatg    7080
atcccccatg ttgtgcaaaa aagcggttag ctccttcggt cctccgatcg ttgtcagaag    7140
taagttggcc gcagtgttat cactcatggt tatggcagca ctgcataatt ctcttactgt    7200
catgccatcc gtaagatgct tttctgtgac tggtgagtac tcaaccaagt cattctgaga    7260
atagtgtatg cggcgaccga gttgctcttg cccggcgtca atacgggata ataccgcgcc    7320
acatagcaga actttaaaag tgctcatcat tggaaaacgt tcttcgggc gaaaactctc      7380 aaggatctta ccgctgttga tccagttc gatgtaaccc actcgtgcac ccaactgatc       7440
ttcagcatct tttactttca ccagcgtttc tgggtgagca aaaacaggaa ggcaaaatgc     7500
cgcaaaaaag ggaataaggg cgacacggaa atgttgaata ctcatactct tcctttttca     7560
atattattga agcatttatc agggttattg tctcatgagc ggatacatat ttgaatgtat    7620
```

| | |
|---|---|
| ttagaaaaat aaacaaatag gggttccgcg cacatttccc cgaaaagtgc cacctaaatt | 7680 |
| gtaagcgtta atattttgtt aaaattcgcg ttaaatttttt gttaaatcag ctcatttttt | 7740 |
| aaccaatagg ccgaaatcgg caaaatccct tataaatcaa agaatagac cgagataggg | 7800 |
| ttgagtgttg ttccagtttg gaacaagagt ccactattaa agaacgtgga ctccaacgtc | 7860 |
| aaagggcgaa aaaccgtcta tcagggcgat ggcccactac gtgaaccatc accctaatca | 7920 |
| agttttttgg ggtcgaggtg ccgtaaagca ctaaatcgga accctaaagg gagcccccga | 7980 |
| tttagagctt gacggggaaa gccggcgaac gtggcgagaa aggaagggaa gaaagcgaaa | 8040 |
| ggagcgggcg ctagggcgct ggcaagtgta gcggtcacgc tgcgcgtaac caccacccc | 8100 |
| gccgcgctta atgcgccgct acagggcgcg tcccattcgc cattcaggct gcgcaactgt | 8160 |
| tgggaagggc gatcggtgcg ggcctcttcg ctattacgcc ag | 8202 |

<210> SEQ ID NO 5
<211> LENGTH: 8202
<212> TYPE: DNA
<213> ORGANISM: artificial sequence
<220> FEATURE:
<223> OTHER INFORMATION: pCS2+_EF1a_RexA_ND_3xFLAG_NLS plasmid

<400> SEQUENCE: 5

| | |
|---|---|
| gtaattcata caaaaggact cgcccctgcc ttggggaatc ccagggaccg tcgttaaact | 60 |
| cccactaacg tagaacccag agatcgctgc gttcccgccc cctcacccgc ccgctctcgt | 120 |
| catcactgag gtggagaaga gcatgcgtga ggctccggtg cccgtcagtg ggcagagcgc | 180 |
| acatcgccca cagtccccga aagttgggg ggaggggtcg gcaattgaac cggtgcctag | 240 |
| agaaggtggc gcggggtaaa ctgggaaagt gatgtcgtgt actggctccg ccttttttccc | 300 |
| gagggtgggg gagaaccgta tataagtgca gtagtcgccg tgaacgttct ttttcgcaac | 360 |
| gggtttgccg ccagaacaca ggtaagtgcc gtgtgtggtt cccgcgggcc tggcctcttt | 420 |
| acgggttatg gcccttgcgt gccttgaatt acttccacgc ccctggctgc agtacgtgat | 480 |
| tcttgatccc gagcttcggg ttggaagtgg gtgggagagt tcgaggcctt gcgcttaagg | 540 |
| agccccttcg cctcgtgctt gagttgaggc ctggcttggg cgctggggcc gccgcgtgcg | 600 |
| aatctggtgg caccttcgcg cctgtctcgc tgctttcgat aagtctctag ccatttaaaa | 660 |
| tttttgatga cctgctgcga cgcttttttt ctggcaagat agtcttgtaa atgcgggcca | 720 |
| agatctgcac actggtatt cggttttgg ggccgcgggc ggcgacgggg cccgtgcgtc | 780 |
| ccagcgcaca tgttcggcga ggcggggcct gcgagcgcgg ccaccgagaa tcggacgggg | 840 |
| gtagtctcaa gctggccggc ctgctctggt gcctggcctc gcgccgccgt gtatcgcccc | 900 |
| gccctgggcg gcaaggctgg cccggtcggc accagttgcg tgagcggaaa gatgccgct | 960 |
| tcccggccct gctgcaggga gctcaaaatg gaggacgcgg cgctcgggag agcgggcggg | 1020 |
| tgagtcaccc acacaaagga aaagggcctt tccgtcctca gccgtcgctt catgtgactc | 1080 |
| cacggagtac cgggcgccgt ccaggcacct cgattagttc tcgagctttt ggagtacgtc | 1140 |
| gtctttaggt tggggggagg ggttttatgc gatggagttt ccccacactg agtgggtgga | 1200 |
| gactgaagtt aggccagctt ggcacttgat gtaattctcc ttggaatttg cccttttga | 1260 |
| gtttggatct tggttcattc tcaagcctca gacagtggtt caaagttttt ttcttccatt | 1320 |
| tcaggtgtcg tgagactcgt ttagtgaacc gtcagatcgc ctggagacgc catccacgct | 1380 |
| gttttgacct ccatagaaga caccgggacc gatccagcct ccgcggcccc gaattcgcca | 1440 |

```
ccatgatatc ttttgctcca ttcctgtccc ccgaggcaat caagcacctc caggaaaacg    1500
aaagatgtag ggatcagtcc caaaaaagaa cggcacagca aatagaggct atctatacga    1560
gtggccagaa catacttgtt agcgcttctg cagggagcgg gaagaccttc gtcatggttg    1620
agagaattct ggacaaaatc ttgagaggcg tatccataga tcggttgttc atttctactt    1680
tcaccgtgaa ggcagccact gagcttcgag agcgcattga aaataaattg tacagccaga    1740
ttgcgcaaac aactgacttt cagatgaagg tatatctgac cgagcaactt cagtctctgt    1800
gtcaagcgga cataggcacg atggatgcat tcgcccagaa agtggtttcc cgatatggct    1860
actccatcgg aatatcctca cagtttcgaa taatgcaaga taaagcagag caagacgttt    1920
tgaagcaaga agtcttttct aagcttttta atgagtttat gaatcaaaaa gaggccccag    1980
tctttcgagc gttggttaaa aatttctctg gaactgcaa agacacctct gcattcagag     2040
aattggtcta cacctgttat agcttagcc aatcaactga aacccgaag atatggttgc     2100 aggaaaattt cctttccgca gcaaaaacgt accagaggct ggaagatatt ccagatcatg    2160
atattgaact cttgcttctt gcaatgcaag atacggcgaa ccaacttcgc gatgtcacgg    2220
acatggagga ctatggtcag ctcactaagg cagggagccg atcagcaaag tacactaagc    2280
accttacgat tatagagaag ctgagcgact gggttaggga ttttaaatgc ctctacggta    2340
aagctggtct ggacagattg atacgggacg ttacaggact gattcctagc ggtaacgatg    2400
ttaccgtgtc taaggtaaag taccctgtat tcaaaaacctt gcaccaaaag cttaagcaat    2460
ttaggcatct ggaaacgatc ctgatgtacc aaaaagactg tttctccctg ctcgaacagt    2520
tgcaagactt tgtattggcc ttttcagagg cttacttggc tgtgaagatt caggaatctg    2580
cgttcgaatt cagtgatatt gctcacttcg cgattaaaat cctggaggaa aataccgata    2640
ttcgccagag ctatcaacag cattatcacg aagtaatggt ggacgagtat caggataata    2700
accatatgca agaacgcctc ctcacactgc tctcaaacgg tcacaacaga tttatggtgg    2760
gtgatattaa gcagtcaatc tatcgattta gacaagccga cccgcaaatt tttaaccaga    2820
agtttcggga ttatcagaaa aagcccgagc agggaaaagt catcctcctg aaagagaatt    2880
tccgctccca gagtgaagtc cttaacgtct caaatgccgt cttttagccac cttatggacg    2940 aaagtgtcgg tgatgtactg tatgacgagc agcatcagtt gattgcagga agccatgccc    3000
aaaccgtccc gtacctcgac agacgcgcgc agctcctcct gtacaattcc gataaagatg    3060
acgggaatgc accgagcgac tctgaaggca taagcttctc tgaagttaca attgtcgcta    3120
aagagatcat caagctgcac aacgataagg gagtaccttt tgaagatatt actctgctcg    3180
tgtcttcccg gaccagaaac gatattatta gccatacatt taaccagtat ggaattccaa    3240
tagctacgga tggggggtcaa cagaattatc tgaaatccgt agaggtgatg gttatgctgg    3300
acacactcag aacgataaat aatccacgga acgactacgc actcgttgca ttgttgaggt    3360
ccccgatgtt tgctttcgac gaggacgact tggcgaggat cgctttgcaa aaagataatg    3420
agctggataa ggactgtctc tatgataaaa ttcagcgagc ggtaatcggc cggggtgcac    3480
accccgagtt gatacacgat accctgcttg ggaaacttaa tgttttcctc aagacattga    3540
aatcttggcg ccggtatgcg aagctcggct ctctctatga cctcatctgg aaaattttta    3600
atgaccgctt ttactttgac ttcgtggcaa gtcaagccaa ggcagaacag gcgcaggcca    3660
acctctatgc gctcgcccct cgggctaacc aatttgaaaa gtcagggtat aaggggttgt    3720
accgcttcat aaagatgatt gataaagtcc ttgaaactca gaatgacttg gcggacgtag    3780
aagtagcgac tccgaagcag gcagttaatc tgatgacaat tcataaaagt aaaggactgc    3840
```

```
aattcccata tgtttttatc ttgaattgcg acaaacgatt tagtatgacg gatatccaca    3900
agtcatttat actgaatagg caacatggta ttggtattaa gtacttggcc gatataaaag    3960
gcttgttggg ggaaacaaca cttaatagcg ttaaggtttc catggagaca ttgccatacc    4020
aactgaacaa gcaagagctc cgactcgcca cactgagtga ggaaatgaga ctcctgtatg    4080
tggcaatgac aagagctgag aagaaggtgt actttatcgg gaaggcctca aaaagtaaaa    4140
gccaagagat tactgatccc aaaaagctgg gtaaattgct tccccttgcg ttgagagagc    4200
agctgctcac atttcaagat tggcttcttg cgattgctga catatttccc actgaagatc    4260
tgtattttga cgtgaggttc attgaagact ccgacctcac tcaagaaagc gtgggtcgat    4320
tgcagactcc tcagctcctc aacccccgacg atctgaaaga caaccggcag tccgagacaa    4380
tagcacgggc attggatatg cttgaagcgg tttcccaact taatgccaat tatgaagcgg    4440
cgatacacct cccaaccgtc agaactccct cacaacttaa ggccacctat gagccgttgc    4500
tggaacccat cggtgtcgac ataattgaga aatcatctag gtctctttcc gactttacac    4560
tcccccactt tagcaaaaag gctaaagtag aagcgtcaca cattggctca gccctccacc    4620
aactcatgca gtcctgcccc ttgagtaagc caatcaacca gcagaccctc ctcgatgccc    4680
ttcgaggcat tgactcaaat gaggaagtca agacagcgtt ggatcttaaa aaaattgagt    4740
cttttttttg cgacacatca ctcggccagt ttttccagac ataccaaaag catctgtata    4800
gagaagcgcc attcgctatt ttgaaactgg atccaataag tcaagaggag tatgtcctga    4860
gagggattat cgatgcgtac tttctgtttg atgatcatat tgtacttgta gcatacaaaa    4920
cggacaaata taaacagcct atcgaactga aaaagcgcta ccaacaacag ttggaactgt    4980
acgcggaggc cctcacccaa acatataaac tccccgtcac aaagagatat ttggttctca    5040
tgggtggtgg caaacctgaa attgtagagg tcggctccgg agactataag gaccacgacg    5100
gagactacaa ggatcatgat attgattaca agacgatga cgataagggc tccggcaaaa    5160
ggccggcggc cacgaaaaag gccggccagg caaaaaagaa aaagtgaatc tagaactata    5220
gtgagtcgta ttacgtagat ccagacatga taagatacat tgatgagttt ggacaaacca    5280
caactagaat gcagtgaaaa aaatgcttta tttgtgaaat ttgtgatgct attgctttat    5340
ttgtaaccat tataagctgc aataaacaag ttaacaacaa caattgcatt cattttatgt    5400
ttcaggttca gggggaggtg tgggaggttt tttaattcgc ggccgcggcg ccaatgcatt    5460
gggcccggta cccagctttt gttcccttta gtgagggtta attgcgcgct tggcgtaatc    5520
atggtcatag ctgtttcctg tgtgaaattg ttatccgctc acaattccac acaacatacg    5580
agccggaagc ataaagtgta aagcctgggg tgcctaatga gtgagctaac tcacattaat    5640
tgcgttgcgc tcactgcccg ctttccagtc gggaaacctg tcgtgccagc tgcattaatg    5700
aatcggccaa cgcgcgggga gaggcggttt gcgtattggg cgctcttccg cttcctcgct    5760
cactgactcg ctgcgctcgg tcgttcggct gcggcgagcg gtatcagctc actcaaaggc    5820
ggtaatacgg ttatccacag aatcagggga taacgcagga aagaacatgt gagcaaaagg    5880
ccagcaaaag gccaggaacc gtaaaaaggc cgcgttgctg gcgttttccc ataggctccg    5940
cccccctgac gagcatcaca aaaatcgacg ctcaagtcag aggtggcgaa acccgacagg    6000
actataaaga taccaggcgt ttccccctgg aagctccctc gtgcgctctc ctgttccgac    6060
cctgccgctt accggatacc tgtccgcctt tctcccttcg ggaagcgtgg cgctttctca    6120
tagctcacgc tgtaggtatc tcagttcggt gtaggtcgtt cgctccaagc tgggctgtgt    6180
```

```
gcacgaaccc cccgttcagc ccgaccgctg cgccttatcc ggtaactatc gtcttgagtc      6240
caacccggta agacacgact tatcgccact ggcagcagcc actggtaaca ggattagcag      6300
agcgaggtat gtaggcggtg ctacagagtt cttgaagtgg tggcctaact acggctacac      6360
tagaaggaca gtatttggta tctgcgctct gctgaagcca gttaccttcg gaaaaagagt      6420
tggtagctct tgatccggca aacaaaccac cgctggtagc ggtggttttt ttgtttgcaa      6480
gcagcagatt acgcgcagaa aaaaggatc tcaagaagat cctttgatct tttctacggg      6540
gtctgacgct cagtggaacg aaaactcacg ttaagggatt ttggtcatga gattatcaaa      6600
aaggatcttc acctagatcc ttttaaatta aaaatgaagt tttaaatcaa tctaaagtat      6660
atatgagtaa acttggtctg acagttacca atgcttaatc agtgaggcac ctatctcagc      6720
gatctgtcta tttcgttcat ccatagttgc ctgactcccc gtcgtgtaga taactacgat      6780
acgggagggc ttaccatctg gccccagtgc tgcaatgata ccgcgagacc cacgctcacc      6840
ggctccagat ttatcagcaa taaaccagcc agccggaagg gccgagcgca gaagtggtcc      6900
tgcaacttta tccgcctcca tccagtctat taattgttgc cgggaagcta gagtaagtag      6960
ttcgccagtt aatagtttgc gcaacgttgt tgccattgct acaggcatcg tggtgtcacg      7020
ctcgtcgttt ggtatggctt cattcagctc cggttcccaa cgatcaaggc gagttacatg      7080
atcccccatg ttgtgcaaaa aagcggttag ctccttcggt cctccgatcg ttgtcagaag      7140
taagttggcc gcagtgttat cactcatggt tatggcagca ctgcataatt ctcttactgt      7200
catgccatcc gtaagatgct tttctgtgac tggtgagtac tcaaccaagt cattctgaga      7260
atagtgtatg cggcgaccga gttgctcttg cccggcgtca atacgggata ataccgcgcc      7320
acatagcaga actttaaaag tgctcatcat tggaaaacgt tcttcggggc gaaaactctc      7380
aaggatctta ccgctgttga gatccagttc gatgtaaccc actcgtgcac ccaactgatc      7440
ttcagcatct tttactttca ccagcgtttc tgggtgagca aaaacaggaa ggcaaaatgc      7500
cgcaaaaaag ggaataaggg cgacacggaa atgttgaata ctcatactct tcctttttca      7560
atattattga agcatttatc agggttattg tctcatgagc ggatacatat ttgaatgtat      7620
ttagaaaaat aaacaaatag gggttccgcg cacatttccc cgaaaagtgc cacctaaatt      7680
gtaagcgtta atattttgtt aaaattcgcg ttaaattttt gttaaatcag ctcatttttt      7740
aaccaatagg ccgaaatcgg caaaatccct tataaatcaa agaatagacc gagataggg      7800 ttgagtgttg ttccagtttg gaacaagagt ccactattaa agaacgtgga ctccaacgtc      7860
aaagggcgaa aaaccgtcta tcagggcgat ggcccactac gtgaaccatc acctaatca      7920 agttttttgg ggtcgaggtg ccgtaaagca ctaaatcgga acctaaagg gagcccccga      7980 tttagagctt gacggggaaa gccggcgaac gtggcgagaa aggaagggaa gaaagcgaaa      8040
ggagcgggcg ctagggcgct ggcaagtgta gcggtcacgc tgcgcgtaac caccacaccc      8100
gccgcgctta atgcgccgct acagggcgcg tcccattcgc cattcaggct gcgcaactgt      8160
tgggaagggc gatcggtgcg ggcctcttcg ctattacgcc ag                        8202
```

<210> SEQ ID NO 6
<211> LENGTH: 7765
<212> TYPE: DNA
<213> ORGANISM: artificial sequence
<220> FEATURE:
<223> OTHER INFORMATION: pCS2+_EF1a_RexB_HA_NLS plasmid

<400> SEQUENCE: 6

```
cctcttcgct attacgccag gtaattcata caaaaggact cgcccctgcc ttggggaatc        60
```

```
ccagggaccg tcgttaaact cccactaacg tagaacccag agatcgctgc gttcccgccc    120
cctcacccgc ccgctctcgt catcactgag gtggagaaga gcatgcgtga ggctccggtg    180
cccgtcagtg ggcagagcgc acatcgccca cagtccccga gaagttgggg ggaggggtcg    240
gcaattgaac cggtgcctag agaaggtggc gcggggtaaa ctgggaaagt gatgtcgtgt    300
actggctccg ccttttttcc gagggtgggg gagaaccgta tataagtgca gtagtcgccg    360
tgaacgttct ttttcgcaac gggtttgccg ccagaacaca ggtaagtgcc gtgtgtggtt    420
cccgcgggcc tggcctcttt acgggttatg gcccttgcgt gccttgaatt acttccacgc    480
ccctggctgc agtacgtgat tcttgatccc gagcttcggg ttggaagtgg gtgggagagt    540
tcgaggcctt gcgcttaagg agccccttcg cctcgtgctt gagttgaggc ctggcttggg    600
cgctggggcc gccgcgtgcg aatctggtgg caccttcgcg cctgtctcgc tgctttcgat    660
aagtctctag ccatttaaaa ttttttgatga cctgctgcga cgcttttttt ctggcaagat    720
agtcttgtaa atgcgggcca agatctgcac actggtattt cggttttggg ggccgcgggc    780
ggcgacgggg cccgtgcgtc ccagcgcaca tgttcggcga ggcggggcct gcgagcgcgg    840
ccaccgagaa tcgacggggg gtagtctcaa gctggccggc ctgctctggt gcctggcctc    900
gcgccgccgt gtatcgcccc gccctgggcg gcaaggctgg cccggtcggc accagttgcg    960
tgagcggaaa gatggccgct tccccggccct gctgcaggga gctcaaaatg gaggacgcgg   1020
cgctcgggag agcgggcggg tgagtcaccc acacaaagga aaagggcctt ccgtcctca    1080 gccgtcgctt catgtgactc cacgagtac cgggcgccgt ccaggcacct cgattagttc    1140
tcgagctttt ggagtacgtc gtctttaggt tgggggagg ggttttatgc gatggagttt    1200
ccccacactg agtgggtgga gactgaagtt aggccagctt ggcacttgat gtaattctcc    1260
ttggaatttg ccctttttga gtttggatct tggttcattc tcaagcctca gacagtggtt    1320
caaagttttt ttcttccatt tcaggtgtcg tgagactcgt ttagtgaacc gtcagatcgc    1380
ctggagacgc catccacgct gttttgacct ccatagaaga caccgggacc gatccagcct    1440
ccgcggcccc gaattcgcca ccatgaagct gatttataca gagatgagtt acagcatgac    1500
ggaaatactc gtcaatgaag caagaaaggc ggctgaccaa ggctacaggg tattctacat    1560
tgcacctaac agtctgagtt ttgaaaagga aagggaggtt ttgaccctcc tgcccgaacg    1620
cggaacgttc agcataattg taaccaggtt tgtacaaatg agtaggtact ttactgtgga    1680
atcatcacca tctaaacagc acctggatga taccacgctt gcaatgatat tctatagagc    1740
actgatgcaa ttgaaacctg aagatctccc gtcatatggt cgactgcaaa acaattcagt    1800
tttcattgag caattggtag agctttataa agagcttaaa aatgctcaac tgagtgtaca    1860
cgatttgacg ggccttgacc acccgcaaaa acaggaggac ctcattaaaa taatagagtt    1920
ggctgaaacc ataatgatac agcaggatta caaccaggat tctccgctcc aaagttttgc    1980
ccgagccatt aagctgggct tgctgaacaa tcagctctca aagacggtgg tcgtgataga    2040
cggattttct aggttcagcg ctgaagaaga ttaccttctt agccttctga caacaattg    2100 ccaggaggta ataatcggct catatgttag tcagaaggcc tatcaaaagt cattcataaa    2160
ggggaatatt tacgaagcct cttttgcactt tcttcaggat ctcgcccaga agtatcacat    2220
caagccagtc tttgcgacta gtaaccaggt ttttaagcct gcattttccc ggctcaccca    2280
gttgtttgag gcgacccatg atttttctca ggtggattgg caattgcaga aaagtgatct    2340
ggaccacttt tcactgtggc aatgccatca tcaaaaagag gaaattgagc acgtcgcaaa    2400
```

-continued

```
gtcaatccga caaaaattgt acgaaggtta tcgctataaa gacatactcg tcttgcttgg    2460
ggatatggac gcttatcagc tccagatcgg cccgatcttc gataagttcg agataccctg    2520
ttacctcggc aaagctgagc ccatggcggc tcacccttg gtgcagttta tagagagtct    2580
cgagaggtca aacgatata actggcgccg agaggatatt ctcaacatgt tgaagagcgg    2640
gctcttcggc tgtttcgacg acagcgacat tgaccgattt gaagagtata ctcaattcgc    2700
agatataaaa ggcttcacaa aattcagtaa acccttaca atcaacagca gccgacaata    2760 tccctcgat ttcttgaacg aaatgcgaca ggatatagtg ttgcccctcc aggaattgtt    2820
taaaagccag aagcagctcg ggcatcact cgtagataag ttgattctgt tttgaagaa    2880 gattcgattg gctgaaaaca tgcaaggctt ggcacagtcc caacttgagg tggagaaaaa    2940
cgaagaggtc tggaaaagat ttactgacat actcacgtct ttccaccata ttttgggca    3000 ggaaaaactc cgattgtctg actgcttggc tctgattaaa acagggatga aagtgcgca    3060 ataccgcgtt gtgcctgcga ctcttgatgt cgttacaata aaatcctatg atctcgtaca    3120
accacattcc aaaccgtttg tatacgcgat aggcttgacg caaagtcact tccctaaaca    3180
aatacatcat agcggtcttt tgtccgacca agagagagcc cgaatcaatg aaatcaggaa    3240
ctaccggcat tttgacatag ctagcgcgga gaattctaaa aagaaccatc agaccgcact    3300
gagcttgttc aacgcagcca ctaaagaact ggttcttagc gtgtcaacag ttattaatga    3360
aacatttgat gatctctcac cttatcttaa ggaactcatt aacttcgggc tcccgctcct    3420
ggacaaggga aaaaactatc tctcttatga taactctgac atagggaact acaaggcgct    3480
tttgtcacag attattgcca ttaatcgaca ggaccttatc gaaatgagtg accaagataa    3540
aatgttttgg acggtagtgc tccgctatct tcggaagcag ttgcggaaac agcaactgga    3600
gctgccaact tccgattaca gactcagcac taagcccttg agcaaagaag tcatcgaagt    3660
ctgtttcccc aaggggatac cgcttaagct ttcagcaacg gctttgactg tgttttacaa    3720
caatcaatat aactatttct tgaaatacgt tctcaacctg aataagaccg agtctataca    3780
tccagacagc agaatacatg gacagtacct tcatagggta ttcgaacgac tgatgaagga    3840
ccacacgcaa gaaccattcg ataacaagct caagcaagcc atttatcaca cgaaccagga    3900
gagcttcttc cagcaagtat accaagacaa cgcggaggcc gaatactctt tggcaatttt    3960
ggaggacatc gtacgctcca ccgcacctat cctgcaactg aaccagaata ttcaagtaat    4020
agaccaagag aaaaatttc agttggatat gggtaacgaa attctggtac acggaattat    4080
tgatcgcatt gatcagctgt ccgacggatc tcttggcatt gtagactaca atcctctgc    4140 gaaccaattt gacatcggta cgttttacaa cgggctgagc ccacaattga tgacatacct    4200
cgcagccctg aagcagatag cacccacga tatcaaccaa ttgttcggcg cgatgtatct    4260
ccacttgcag gacccgaaac ttgaccttgt aacctttaaa cagatcgata acacattggt    4320
tgagtctatt tacaaggctc tcacttacaa agggatattt agtgaagtag agaaagagca    4380
tctttctaca ggcgcatacc agacgaagaa tcgttgtat agcaacgatg agcttgagac    4440
tttgctcaat tacaacaagt acctttacct caaagcagcc aagcatataa agaaggggca    4500
tttcctcatc aatccgtaca cgtctgatgg caaaacagtt caaggcgacc aactcaaagc    4560
tatcacccgc ttcgaagccg acttggacat ggggcaggct cggagactgg tgacactgcc    4620
tgctaaagag aaaaaagagt gcttcctgac cctcatgagg aaggagtccc atcttggctc    4680
cggataccca tacgatgttc cagattacgc tggctccggc aaaaggccgg cggccacgaa    4740
aaaggccggc caggcaaaaa agaaaaagta gtctagaact atagtgagtc gtattacgta    4800
```

```
gatccagaca tgataagata cattgatgag tttggacaaa ccacaactag aatgcagtga   4860
aaaaaatgct ttatttgtga aatttgtgat gctattgctt tatttgtaac cattataagc   4920
tgcaataaac aagttaacaa caacaattgc attcatttta tgtttcaggt tcaggggagg   4980
gtgtgggagg tttttttaatt cgcggccgcg cgccaatgc attgggcccg gtacccagct   5040
tttgttccct ttagtgaggg ttaattgcgc gcttggcgta atcatggtca tagctgtttc   5100
ctgtgtgaaa ttgttatccg ctcacaattc cacacaacat acgagccgga agcataaagt   5160
gtaaagcctg gggtgcctaa tgagtgagct aactcacatt aattgcgttg cgctcactgc   5220
ccgcttccca gtcgggaaac ctgtcgtgcc agctgcatta atgaatcggc caacgcgcgg   5280
ggagaggcgg tttgcgtatt gggcgctctt ccgcttcctc gctcactgac tcgctgcgct   5340
cggtcgttcg gctgcggcga gcggtatcag ctcactcaaa ggcggtaata cggttatcca   5400
cagaatcagg ggataacgca ggaaagaaca tgtgagcaaa aggccagcaa aaggccagga   5460
accgtaaaaa ggccgcgttg ctggcgtttt tccataggct ccgcccccct gacgagcatc   5520
acaaaaatcg acgctcaagt cagaggtggc gaaacccgac aggactataa agataccagg   5580
cgtttccccc tggaagctcc ctcgtgcgct ctcctgttcc gaccctgccg cttaccggat   5640
acctgtccgc ctttctccct tcgggaagcg tggcgctttc tcatagctca cgctgtaggt   5700
atctcagttc ggtgtaggtc gttcgctcca agctgggctg tgtgcacgaa ccccccgttc   5760
agcccgaccg ctgcgcctta tccggtaact atcgtcttga gtccaacccg gtaagacacg   5820
acttatcgcc actggcagca gccactggta acaggattag cagagcgagg tatgtaggcg   5880
gtgctacaga gttcttgaag tggtggccta actacggcta cactagaagg acagtatttg   5940
gtatctgcgc tctgctgaag ccagttacct tcggaaaaag agttggtagc tcttgatccg   6000
gcaaacaaac caccgctggt agcggtggtt tttttgtttg caagcagcag attacgcgca   6060
gaaaaaaagg atctcaagaa gatcctttga tcttttctac ggggtctgac gctcagtgga   6120
acgaaaactc acgttaaggg attttggtca tgagattatc aaaaaggatc ttcacctaga   6180
tccttttaaa ttaaaaatga agttttaaat caatctaaag tatatatgag taaacttggt   6240
ctgacagtta ccaatgctta atcagtgagg cacctatctc agcgatctgt ctatttcgtt   6300
catccatagt tgcctgactc cccgtcgtgt agataactac gatacgggag ggcttaccat   6360
ctggccccag tgctgcaatg ataccgcgag acccacgctc accggctcca gatttatcag   6420
caataaacca gccagccgga agggccgagc gcagaagtgg tcctgcaact ttatccgcct   6480
ccatccagtc tattaattgt tgccgggaag ctagagtaag tagttcgcca gttaatagtt   6540
tgcgcaacgt tgttgccatt gctacaggca tcgtggtgtc acgctcgtcg tttggtatgg   6600
cttcattcag ctccggttcc caacgatcaa ggcgagttac atgatccccc atgttgtgca   6660
aaaaagcggt tagctccttc ggtcctccga tcgttgtcag aagtaagttg gccgcagtgt   6720
tatcactcat ggttatggca gcactgcata attctcttac tgtcatgcca tccgtaagat   6780
gcttttctgt gactggtgag tactcaacca agtcattctg agaatagtgt atgcggcgac   6840
cgagttgctc ttgcccggcg tcaatacggg ataataccgc gccacatagc agaactttaa   6900
aagtgctcat cattggaaaa cgttcttcgg ggcgaaaact ctcaaggatc ttaccgctgt   6960
tgagatccag ttcgatgtaa ccactcgtg cacccaactg atcttcagca tcttttactt   7020
tcaccagcgt ttctgggtga gcaaaaacag gaaggcaaaa tgccgcaaaa aagggaataa   7080
gggcgacacg gaaatgttga atactcatac tcttcctttt tcaatattat tgaagcattt   7140
```

```
atcagggtta ttgtctcatg agcggataca tatttgaatg tatttagaaa aataaacaaa    7200
taggggttcc gcgcacattt ccccgaaaag tgccacctaa attgtaagcg ttaatatttt    7260
gttaaaattc gcgttaaatt tttgttaaat cagctcattt tttaaccaat aggccgaaat    7320
cggcaaaatc ccttataaat caaaagaata gaccgagata gggttgagtg ttgttccagt    7380
ttggaacaag agtccactat taaagaacgt ggactccaac gtcaaagggc gaaaaaccgt    7440
ctatcagggc gatggcccac tacgtgaacc atcaccctaa tcaagttttt tggggtcgag    7500
gtgccgtaaa gcactaaatc ggaaccctaa agggagcccc gatttagag cttgacgggg     7560
aaagccggcg aacgtggcga aaggaagg gaagaaagcg aaaggagcgg gcgctagggc      7620
gctggcaagt gtagcggtca cgctgcgcgt aaccaccaca cccgccgcgc ttaatgcgcc    7680
gctacagggc gcgtcccatt cgccattcag gctgcgcaac tgttgggaag ggcgatcggt    7740
gcgggcctct tcgctattac gccag                                         7765
```

<210> SEQ ID NO 7
<211> LENGTH: 7765
<212> TYPE: DNA
<213> ORGANISM: artificial sequence
<220> FEATURE:
<223> OTHER INFORMATION: pCS2+_EF1a_RexB_ND_HA_NLS plasmid

<400> SEQUENCE: 7

```
cctcttcgct attacgccag gtaattcata caaaaggact cgcccctgcc ttggggaatc      60
ccagggaccg tcgttaaact cccactaacg tagaacccag agatcgctgc gttcccgccc     120
cctcacccgc ccgctctcgt catcactgag gtggagaaga gcatgcgtga ggctccggtg     180
cccgtcagtg ggcagagcgc acatcgccca cagtccccga aagttggggg gaggggtcg      240
gcaattgaac cggtgcctag agaaggtggc gcggggtaaa ctgggaaagt gatgtcgtgt     300
actggctccg cctttttccc gagggtgggg gagaaccgta tataagtgca gtagtcgccg     360
tgaacgttct ttttcgcaac gggtttgccg ccagaacaca ggtaagtgcc gtgtgtggtt     420
cccgcgggcc tggcctctt acgggttatg gcccttgcgt gccttgaatt acttccacgc     480
ccctggctgc agtacgtgat tcttgatccc gagcttcggg ttggaagtgg gtgggagagt    540
tcgaggcctt gcgcttaagg agccccttcg cctcgtgctt gagttgaggc ctggcttggg    600
cgctggggcc gccgcgtgcg aatctggtgg caccttcgcg cctgtctcgc tgctttcgat     660
aagtctctag ccatttaaaa ttttttgatga cctgctgcga cgcttttttt ctggcaagat    720
agtcttgtaa atgcgggcca agatctgcac actggtattt cggttttgg ggccgcgggc     780
ggcgacgggg cccgtgcgtc ccagcgcaca tgttcggcga ggcggggcct gcgagcgcgg    840
ccaccgagaa tcggacgggg gtagtctcaa gctggccggc ctgctctggt gcctggcctc    900
gcgccgccgt gtatcgcccc gccctgggcg gcaaggctgg cccggtcggc accagttgcg    960
tgagcggaaa gatggccgct tcccggccct gctgcaggga gctcaaaatg gaggacgcgg   1020
cgctcgggag agcgggcggg tgagtcaccc acacaaagga aaagggcctt tccgtcctca   1080
gccgtcgctt catgtgactc cacggagtac cgggcgccgt ccaggcacct cgattagttc   1140
tcgagctttt ggagtacgtc gtcttttaggt tgggggagg ggtttatgc gatgagtttt     1200
ccccacactg agtgggtgga gactgaagtt aggccagctt ggcacttgat gtaattctcc   1260
ttggaatttg cccttttttga gttggatct tggttcattc tcaagcctca gacagtggtt    1320
caaagttttt ttcttccatt tcaggtgtcg tgagactcgt ttagtgaacc gtcagatcgc    1380
ctggagacgc catccacgct gttttgacct ccatagaaga caccgggacc gatccagcct   1440
```

```
ccgcggcccc gaattcgcca ccatgaagct gatttataca gagatgagtt acagcatgac    1500
ggaaatactc gtcaatgaag caagaaaggc ggctgaccaa ggctacaggg tattctacat    1560
tgcacctaac agtctgagtt ttgaaaagga aagggaggtt ttgaccctcc tgcccgaacg    1620
cggaacgttc agcataattg taaccaggtt tgtacaaatg agtaggtact ttactgtgga    1680
atcatcacca tctaaacagc acctggatga taccacgctt gcaatgatat tctatagagc    1740
actgatgcaa ttgaaacctg aagatctccc gtcatatggt cgactgcaaa acaattcagt    1800
tttcattgag caattggtag agctttataa agagcttaaa aatgctcaac tgagtgtaca    1860
cgatttgacg ggccttgacc acccgcaaaa acaggaggac ctcattaaaa taatagagtt    1920
ggctgaaacc ataatgatac agcaggatta caaccaggat tctccgctcc aaagttttgc    1980
ccgagccatt aagctgggct tgctgaacaa tcagctctca aagacggtgg tcgtgataga    2040
cggattttct aggttcagcg ctgaagaaga ttaccttctt agccttctga caacaattg     2100 ccaggaggta ataatcggct catatgttag tcagaaggcc tatcaaaagt cattcataaa    2160
ggggaatatt tacgaagcct ctttgcactt tcttcaggat ctcgcccaga gtatcacat     2220 caagccagtc tttgcgacta gtaaccaggt ttttaagcct gcattttccc ggctcaccca    2280
gttgtttgag gcgacccatg attttttctca ggtggattgg caattgcaga aaagtgatct    2340
ggaccacttt tcactgtggc aatgccatca tcaaaaagag gaaattgagc acgtcgcaaa    2400
gtcaatccga caaaaattgt acgaaggtta tcgctataaa gacatactcg tcttgcttgg    2460
ggatatggac gcttatcagc tccagatcgg cccgatcttc gataagttcg agatacccta    2520
ttacctcggc aaagctgagc ccatggcggc tcacccttttg gtgcagtttta tagagagtct    2580 cgagaggtca caacgatata actggcgccg agaggatatt ctcaacatgt tgaagagcgg    2640
gctcttcggc tgtttcgacg cagcgacat tgaccgattt gaagagtata ctcaattcgc      2700
agatataaaa ggcttcacaa aattcagtaa acccctttaca atcaacagca gccgacaata    2760
tcccctcgat ttcttgaacg aaatgcgaca ggatatagtg ttgcccctcc aggaattgtt    2820
taaaagccag aagcagctcg ggcatcact cgtagataag ttgattctgt ttttgaagaa    2880
gattcgattg gctgaaaaca tgcaaggctt ggcacagtcc caacttgagg tggagaaaaa    2940
cgaagaggtc tggaaaagat ttactgacat actcacgtct ttccaccata ttttttgggca    3000 ggaaaaactc cgattgtctg actgcttggc tctgattaaa acagggatga aaagtgcgca    3060
ataccgcgtt gtgcctgcga ctcttgatgt cgttacaata aaatcctatg atctcgtaca    3120
accacattcc aaaccgtttg tatacgcgat aggcttgacg caaagtcact ccctaaaca    3180 aatacatcat agcggtcttt tgtccgacca agagagagcc cgaatcaatg aaatcaggaa    3240
ctaccggcat tttgacatag ctagcgcgga gaattctaaa aagaaccatc agaccgcact    3300
gagcttgttc aacgcagcca ctaaagaact ggttcttagc gtgtcaacag ttattaatga    3360
aacatttgat gatctctcac cttatcttaa ggaactcatt aacttcgggc tcccgctcct    3420
ggacaaggga aaaactatc tctcttatga taactctgac atagggaact acaaggcgct    3480
tttgtcacag attattgcca ttaatcgaca ggaccttatc gaaatgagtg accaagataa    3540
aatgttttgg acggtagtgc tccgctatct tcggaagcag ttgcggaaac agcaactgga    3600
gctgccaact tccgattaca gactcagcac taagcccttg agcaaagaag tcatcgaagt    3660
ctgttttccc aagggggatac cgcttaagct ttcagcaacg gctttgactg tgttttacaa    3720
caatcaatat aactatttct tgaaatacgt tctcaacctg aataagaccg agtctataca    3780
```

-continued

```
tccagacagc agaatacatg acagtacct  tcatagggta ttcgaacgac tgatgaagga    3840
ccacacgcaa gaaccattcg ataacaagct caagcaagcc atttatcaca cgaaccagga    3900
gagcttcttc cagcaagtat accaagacaa cgcggaggcc gaatactctt tggcaatttt    3960
ggaggacatc gtacgctcca ccgcacctat cctgcaactg aaccagaata ttcaagtaat    4020
agaccaagag aaaaatttc agttggatat gggtaacgaa attctggtac acggaattat     4080
tgatcgcatt gatcagctgt ccgacggatc tcttggcatt gtagcataca aatcctctgc    4140
gaaccaattt gacatcggta cgttttacaa cgggctgagc ccacaattga tgacatacct    4200
cgcagccctg aagcagatag cacccacga tatcaaccaa ttgttcggcg cgatgtatct     4260
ccacttgcag gacccgaaac ttgaccttgt aacctttaaa cagatcgata acacattggt    4320
tgagtctatt tacaaggctc tcacttacaa agggatattt agtgaagtag agaaagagca    4380
tctttctaca ggcgcatacc agacgaagaa tgcgttgtat agcaacgatg agcttgagac    4440
tttgctcaat tacaacaagt acctttacct caaagcagcc aagcatataa agaaggggca    4500
tttcctcatc aatccgtaca cgtctgatgg caaaacagtt caaggcgacc aactcaaagc    4560
tatcacccgc ttcgaagccg acttggacat ggggcaggct cggagactgg tgacactgcc    4620
tgctaaagag aaaaaagagt gcttcctgac cctcatgagg aaggagtccc atcttggctc    4680 cggatacca  tacgatgttc cagattacgc tggctccggc aaaaggccgg cggccacgaa     4740
aaaggccggc caggcaaaaa agaaaaagta gtctagaact atagtgagtc gtattacgta    4800
gatccagaca tgataagata cattgatgag tttggacaaa ccacaactag aatgcagtga    4860
aaaaaatgct ttatttgtga aatttgtgat gctattgctt tatttgtaac cattataagc    4920
tgcaataaac aagttaacaa caacaattgc attcatttta tgtttcaggt tcaggggag    4980 gtgtgggagg ttttttaatt cgcggccgcg cgccaatgc  attgggcccg gtacccagct    5040
tttgttccct ttagtgaggg ttaattgcgc gcttggcgta atcatggtca tagctgtttc    5100
ctgtgtgaaa ttgttatccg ctcacaattc cacacaacat acgagccgga agcataaagt    5160
gtaaagcctg gggtgcctaa tgagtgagct aactcacatt aattgcgttg cgctcactgc    5220
ccgctttcca gtcgggaaac ctgtcgtgcc agctgcatta atgaatcggc caacgcgcgg    5280
ggagaggcgg tttgcgtatt gggcgctctt ccgcttcctc gctcactgac tcgctgcgct    5340
cggtcgttcg gctgcggcga gcggtatcag ctcactcaaa ggcggtaata cggttatcca    5400
cagaatcagg ggataacgca ggaaagaaca tgtgagcaaa aggccagcaa aaggccagga    5460
accgtaaaaa ggccgcgttg ctggcgtttt tccataggct ccgcccccct gacgagcatc    5520
acaaaaatcg acgctcaagt cagaggtggc gaaacccgac aggactataa agataccagg    5580
cgtttccccc tggaagctcc ctcgtgcgct ctcctgttcc gaccctgccg cttaccggat    5640
acctgtccgc ctttctccct tcgggaagcg tggcgctttc tcatagctca cgctgtaggt    5700
atctcagttc ggtgtaggtc gttcgctcca agctgggctg tgtgcacgaa ccccccgttc    5760
agcccgaccg ctgcgcctta tccggtaact atcgtcttga gtccaacccg gtaagacacg    5820
acttatcgcc actggcagca gccactggta acaggattag cagagcgagg tatgtaggcg    5880
gtgctacaga gttcttgaag tggtggccta actacggcta cactagaagg acagtatttg    5940
gtatctgcgc tctgctgaag ccagttacct tcggaaaaag agttggtagc tcttgatccg    6000
gcaaacaaac caccgctggt agcggtggtt tttttgtttg caagcagcag attacgcgca    6060
gaaaaaaagg atctcaagaa gatcctttga tcttttctac ggggtctgac gctcagtgga    6120
acgaaaactc acgttaaggg attttggtca tgagattatc aaaaaggatc ttcacctaga    6180
```

```
tccttttaaa ttaaaaatga agttttaaat caatctaaag tatatatgag taaacttggt    6240
ctgacagtta ccaatgctta atcagtgagg cacctatctc agcgatctgt ctatttcgtt    6300
catccatagt tgcctgactc cccgtcgtgt agataactac gatacgggag ggcttaccat    6360
ctggccccag tgctgcaatg ataccgcgag acccacgctc accggctcca gatttatcag    6420
caataaacca gccagccgga agggccgagc gcagaagtgg tcctgcaact ttatccgcct    6480
ccatccagtc tattaattgt tgccgggaag ctagagtaag tagttcgcca gttaatagtt    6540
tgcgcaacgt tgttgccatt gctacaggca tcgtggtgtc acgctcgtcg tttggtatgg    6600
cttcattcag ctccggttcc caacgatcaa ggcgagttac atgatccccc atgttgtgca    6660
aaaaagcggt tagctccttc ggtcctccga tcgttgtcag aagtaagttg gccgcagtgt    6720
tatcactcat ggttatggca gcactgcata attctcttac tgtcatgcca tccgtaagat    6780
gcttttctgt gactggtgag tactcaacca agtcattctg agaatagtgt atgcggcgac    6840
cgagttgctc ttgcccggcg tcaatacggg ataataccgc gccacatagc agaactttaa    6900
aagtgctcat cattggaaaa cgttcttcgg ggcgaaaact ctcaaggatc ttaccgctgt    6960
tgagatccag ttcgatgtaa cccactcgtg cacccaactg atcttcagca tcttttactt    7020
tcaccagcgt ttctgggtga gcaaaaacag gaaggcaaaa tgccgcaaaa aagggaataa    7080
gggcgacacg gaaatgttga atactcatac tcttcctttt tcaatattat tgaagcattt    7140
atcagggtta ttgtctcatg agcggataca tatttgaatg tatttagaaa aataaacaaa    7200
taggggttcc gcgcacattt ccccgaaaag tgccacctaa attgtaagcg ttaatatttt    7260
gttaaaattc gcgttaaatt tttgttaaat cagctcattt tttaaccaat aggccgaaat    7320
cggcaaaatc ccttataaat caaaagaata gaccgagata gggttgagtg ttgttccagt    7380
ttggaacaag agtccactat taaagaacgt ggactccaac gtcaagggc gaaaaaccgt    7440 ctatcagggc gatggcccac tacgtgaacc atcaccctaa tcaagttttt tggggtcgag    7500
gtgccgtaaa gcactaaatc ggaaccctaa agggagcccc cgatttagag cttgacgggg    7560
aaagccggcg aacgtggcga gaaaggaagg gaagaaagcg aaaggagcgg cgctagggc    7620 gctggcaagt gtagcggtca cgctgcgcgt aaccaccaca cccgccgcgc ttaatgcgcc    7680
gctacagggc gcgtcccatt cgccattcag gctgcgcaac tgttgggaag ggcgatcggt    7740
gcgggcctct tcgctattac gccag                                          7765

<210> SEQ ID NO 8
<211> LENGTH: 3477
<212> TYPE: DNA
<213> ORGANISM: S. aureus

<400> SEQUENCE: 8
atgacattac atgcttattt aggtagagcg ggaacaggta agtctacgaa aatgttgacc      60
gaaataaaac aaaaaatgaa agcagatccg cttggagatc caatcatttt aattgcgcca     120
actcaaagta catttcaatt agaacaagcc tttgtcaatg atccggaatt aaatggtagt     180
ttaagaacag aagtgttgca ttttgaacga ttaagtcatc gtattttcca agaagttggt     240
agttatagcg aacaaaagtt atctaaagct gcaacgaaa tgatgattta aacattgtt     300 caagaacaac aaaagtattt aaaactttat caatcacaag caaaatatta tgggtttagt     360
gaaaaattaa cagaacaaat tcaagatttt aaaaaatatg cagtaacgcc tgaacattta     420
gaacacttta ttgctgataa aaatatgcaa actcgaacta aaaataagtt agaggatatt     480
```

```
gctttaatat accgtgagtt cgaacaacgc attcaaaacg agtttattac gggtgaggat      540
tcattacaat attttattga ttgtatgccg aaatcagagt ggctaaaacg tgctgatata      600
tatattgatg gttttcacaa cttttcaacg attgagtatt aataatcaa aggattaatt      660 aaatatgcga agagtgtcac aattatattg acgacagatg gtaaccacga tcaatttagt      720
ttatttagaa aaccatcgga agtgttacga catattgaag aaatagcaaa tgaactcaat      780
atttctattg aacgtcaata tttcaaccaa ttatatcgct tcaataatca agatttaaag      840
catcttgaac aagaatttga tgcacttcaa atcaatcgag tggcatgtca aggtcatatc      900
aatattttag aatctgcgac tatgagagag gaaataaatg aaattgcgcg acgtatcatc      960
gttgatattc gtgataagca attacgatat caagatattg ctattttata tcgtgatgaa     1020
tcttatgctt atttatttga ttccatatta ccgctttata atattcctta taatattgat     1080
acaaagcgtt cgatgacaca tcatccggtc atggaaatga ttcgttcatt gattgaagtt     1140
attcaatcta attggcaagt gaatccaatg ctacgcttat tgaagactga tgtgttaacg     1200
gcatcatatc taaaaagtgc atacttagtt gatttacttg aaaattttgt acttgaacgt     1260
ggtatatacg gtaaacgttg gttagatgat gagctatttta atgtcgaaca ttttagcaaa     1320
atggggcgta aagcgcataa actgaccgaa gatgaacgta acacatttga acaagtcgtt     1380
aagttaaaga aagatgtcat tgataaaatt ttacattttg aaaagcaaat gtcacaagcg     1440
gaaactgtaa aagattttgc aactgctttt tatgaaagta tggaatattt cgaactgcca     1500
aatcaattga tgacagagcg agatgaactt gatttaaatg gtaatcatga aaaggcggag     1560
gaaattgatc aaatatggaa tggcttaatt caaatccttg atgacttagt tctagtattt     1620
ggagatgaac caatgtcgat ggaacgtttc ttagaagtat ttgatattgg tttagaacaa     1680
ttagaatttg ttatgattcc gcaaacattg gaccaagtaa gtattggtac gatggatttg     1740
gctaaagtcg ataataagca acatgtttac ttagtaggta tgaatgatgg aacgatgcca     1800
caaccagtaa ctgcgtcaag cttgattaca gatgaagaaa agaaatactt tgaacagcag     1860
gctaatgtcg agttaagtcc aacatcagat attttacaga tggatgaagc atttgtttgt     1920
tatgttgcta tgactagagc taagggagat gttacatttt cttacagtct aatgggatca     1980
agtggtgatg ataaggagat cagcccattt ttaaatcaaa ttcaatcatt gttcaaccaa     2040
ttggaaatta ctaacattcc tcaataccat gaagttaacc cattgtcact aatgcaacat     2100
gctaagcaaa ccaaaattac attatttgaa gcattgcgtg cttggttata tgatgaaatt     2160
gtggctgata gttggttaga tgcttatcaa gtaattagag atagcgatca tttaaatcaa     2220
ggtttagatt atttaatgtc agcattaacg tttgacaatg aaactgtaaa attaggtgaa     2280
acgttgtcta aagatttata tggtaaggaa atcaatgcca gtgtatcccg ttttgaaggt     2340
tatcaacaat gcccatttaa acactatgcg tcacatggtc tgaaactaaa tgagcgaacg     2400
aagtatgaac ttcaaaactt tgatttaggt gatattttcc attctgtttt aaaatatata     2460
tctgaacgta ttaatggcga ttttaaacaa ttagacctga aaaaaataag acaattaacg     2520
aatgaagcat tggaagaaat tttacctaaa gttcagttta attattaaa ttcttcagct     2580 tactatcgtt atttatcaag acgcattggc gctattgtag aaacaacact aagcgcatta     2640
aaatatcaag gcacgtattc aaagtttatg ccaaaacatt ttgagacaag ttttagaagg     2700
aaaccaagaa caaatgacga attaattgca caaacattaa cgacaactca aggtattcca     2760
attaatatta gagggcaaat tgaccgtatc gatacgtata caaagaatga tacaagtttt     2820
gttaatatca ttgactataa atcctctgaa ggtagtgcga cacttgattt aacgaaagta     2880
```

-continued

```
tattatggta tgcaaatgca aatgatgaca tacatggata tcgttttaca aaataaacaa    2940
cgccttggat taacagatat tgtgaaacca ggtggattat tatacttcca tgtacatgaa    3000
cctagaatta aatttaaatc atggtctgat attgatgaag ataaactaga caagattta    3060 attaaaaagt ttaagttgag tggtttagtt aatgcagacc aaactgttat tgatgcattg    3120
gatattcgtt tagaacctaa attcacttca gatattgtac cagttggttt gaataaagat    3180
ggctctttga gtaaacgagg cagccaagtg gcagatgaag caacgattta taaattcatc    3240
caacataaca aagagaattt tatagaaaca gcttcaaata ttatggatgg acatactgaa    3300
gttgcaccat taaagtacaa acaaaaattg ccatgtgctt tttgtagtta tcaatcggta    3360
tgtcatgtag atggcatgat tgatagtaag cgatatcgaa ctgtagatga aacaataaat    3420
ccaattgaag caattcaaaa tattaacatt aatgatgaat ttggggggtga gcaatag    3477
```

<210> SEQ ID NO 9
<211> LENGTH: 1158
<212> TYPE: PRT
<213> ORGANISM: S. aureus

<400> SEQUENCE: 9

```
Met Thr Leu His Ala Tyr Leu Gly Arg Ala Gly Thr Gly Lys Ser Thr
1               5                   10                  15

Lys Met Leu Thr Glu Ile Lys Gln Lys Met Lys Ala Asp Pro Leu Gly
            20                  25                  30

Asp Pro Ile Ile Leu Ile Ala Pro Thr Gln Ser Thr Phe Gln Leu Glu
        35                  40                  45

Gln Ala Phe Val Asn Asp Pro Glu Leu Asn Gly Ser Leu Arg Thr Glu
    50                  55                  60

Val Leu His Phe Glu Arg Leu Ser His Arg Ile Phe Gln Glu Val Gly
65                  70                  75                  80

Ser Tyr Ser Glu Gln Lys Leu Ser Lys Ala Ala Thr Glu Met Met Ile
                85                  90                  95

Tyr Asn Ile Val Gln Glu Gln Lys Tyr Leu Lys Leu Tyr Gln Ser
            100                 105                 110

Gln Ala Lys Tyr Tyr Gly Phe Ser Glu Lys Leu Thr Glu Gln Ile Gln
        115                 120                 125

Asp Phe Lys Lys Tyr Ala Val Thr Pro Glu His Leu Glu His Phe Ile
    130                 135                 140

Ala Asp Lys Asn Met Gln Thr Arg Thr Lys Asn Lys Leu Glu Asp Ile
145                 150                 155                 160

Ala Leu Ile Tyr Arg Glu Phe Glu Gln Arg Ile Gln Asn Glu Phe Ile
                165                 170                 175

Thr Gly Glu Asp Ser Leu Gln Tyr Phe Ile Asp Cys Met Pro Lys Ser
            180                 185                 190

Glu Trp Leu Lys Arg Ala Asp Ile Tyr Ile Asp Gly Phe His Asn Phe
        195                 200                 205

Ser Thr Ile Glu Tyr Leu Ile Ile Lys Gly Leu Ile Lys Tyr Ala Lys
    210                 215                 220

Ser Val Thr Ile Ile Leu Thr Thr Asp Gly Asn His Asp Gln Phe Ser
225                 230                 235                 240

Leu Phe Arg Lys Pro Ser Glu Val Leu Arg His Ile Glu Glu Ile Ala
                245                 250                 255

Asn Glu Leu Asn Ile Ser Ile Glu Arg Gln Tyr Phe Asn Gln Leu Tyr
            260                 265                 270
```

```
Arg Phe Asn Asn Gln Asp Leu Lys His Leu Glu Gln Glu Phe Asp Ala
    275                 280                 285
Leu Gln Ile Asn Arg Val Ala Cys Gln Gly His Ile Asn Ile Leu Glu
290                 295                 300
Ser Ala Thr Met Arg Glu Ile Asn Glu Ile Ala Arg Arg Ile Ile
305                 310                 315                 320
Val Asp Ile Arg Asp Lys Gln Leu Arg Tyr Gln Asp Ile Ala Ile Leu
            325                 330                 335
Tyr Arg Asp Glu Ser Tyr Ala Tyr Leu Phe Asp Ser Ile Leu Pro Leu
                340                 345                 350
Tyr Asn Ile Pro Tyr Asn Ile Asp Thr Lys Arg Ser Met Thr His His
            355                 360                 365
Pro Val Met Glu Met Ile Arg Ser Leu Ile Glu Val Ile Gln Ser Asn
    370                 375                 380
Trp Gln Val Asn Pro Met Leu Arg Leu Leu Lys Thr Asp Val Leu Thr
385                 390                 395                 400
Ala Ser Tyr Leu Lys Ser Ala Tyr Leu Val Asp Leu Leu Glu Asn Phe
                405                 410                 415
Val Leu Glu Arg Gly Ile Tyr Gly Lys Arg Trp Leu Asp Asp Glu Leu
            420                 425                 430
Phe Asn Val Glu His Phe Ser Lys Met Gly Arg Lys Ala His Lys Leu
    435                 440                 445
Thr Glu Asp Glu Arg Asn Thr Phe Glu Gln Val Val Lys Leu Lys Lys
    450                 455                 460
Asp Val Ile Asp Lys Ile Leu His Phe Glu Lys Gln Met Ser Gln Ala
465                 470                 475                 480
Glu Thr Val Lys Asp Phe Ala Thr Ala Phe Tyr Glu Ser Met Glu Tyr
                485                 490                 495
Phe Glu Leu Pro Asn Gln Leu Met Thr Glu Arg Asp Glu Leu Asp Leu
            500                 505                 510
Asn Gly Asn His Glu Lys Ala Glu Glu Ile Asp Gln Ile Trp Asn Gly
        515                 520                 525
Leu Ile Gln Ile Leu Asp Asp Leu Val Leu Val Phe Gly Asp Glu Pro
    530                 535                 540
Met Ser Met Glu Arg Phe Leu Glu Val Phe Asp Ile Gly Leu Glu Gln
545                 550                 555                 560
Leu Glu Phe Val Met Ile Pro Gln Thr Leu Asp Gln Val Ser Ile Gly
                565                 570                 575
Thr Met Asp Leu Ala Lys Val Asp Asn Lys Gln His Val Tyr Leu Val
            580                 585                 590
Gly Met Asn Asp Gly Thr Met Pro Gln Pro Val Thr Ala Ser Ser Leu
        595                 600                 605
Ile Thr Asp Glu Glu Lys Lys Tyr Phe Glu Gln Gln Ala Asn Val Glu
    610                 615                 620
Leu Ser Pro Thr Ser Asp Ile Leu Gln Met Asp Glu Ala Phe Val Cys
625                 630                 635                 640
Tyr Val Ala Met Thr Arg Ala Lys Gly Asp Val Thr Phe Ser Tyr Ser
                645                 650                 655
Leu Met Gly Ser Ser Gly Asp Asp Lys Glu Ile Ser Pro Phe Leu Asn
            660                 665                 670
Gln Ile Gln Ser Leu Phe Asn Gln Leu Glu Ile Thr Asn Ile Pro Gln
    675                 680                 685
```

```
Tyr His Glu Val Asn Pro Leu Ser Leu Met Gln His Ala Lys Gln Thr
        690                 695                 700
Lys Ile Thr Leu Phe Glu Ala Leu Arg Ala Trp Leu Tyr Asp Glu Ile
705                 710                 715                 720
Val Ala Asp Ser Trp Leu Asp Ala Tyr Gln Val Ile Arg Asp Ser Asp
                725                 730                 735
His Leu Asn Gln Gly Leu Asp Tyr Leu Met Ser Ala Leu Thr Phe Asp
            740                 745                 750
Asn Glu Thr Val Lys Leu Gly Glu Thr Leu Ser Lys Asp Leu Tyr Gly
        755                 760                 765
Lys Glu Ile Asn Ala Ser Val Ser Arg Phe Glu Gly Tyr Gln Gln Cys
770                 775                 780
Pro Phe Lys His Tyr Ala Ser His Gly Leu Lys Leu Asn Glu Arg Thr
785                 790                 795                 800
Lys Tyr Glu Leu Gln Asn Phe Asp Leu Gly Asp Ile Phe His Ser Val
                805                 810                 815
Leu Lys Tyr Ile Ser Glu Arg Ile Asn Gly Asp Phe Lys Gln Leu Asp
            820                 825                 830
Leu Lys Lys Ile Arg Gln Leu Thr Asn Glu Ala Leu Glu Glu Ile Leu
        835                 840                 845
Pro Lys Val Gln Phe Asn Leu Leu Asn Ser Ser Ala Tyr Tyr Arg Tyr
850                 855                 860
Leu Ser Arg Arg Ile Gly Ala Ile Val Glu Thr Thr Leu Ser Ala Leu
865                 870                 875                 880
Lys Tyr Gln Gly Thr Tyr Ser Lys Phe Met Pro Lys His Phe Glu Thr
                885                 890                 895
Ser Phe Arg Arg Lys Pro Arg Thr Asn Asp Glu Leu Ile Ala Gln Thr
            900                 905                 910
Leu Thr Thr Thr Gln Gly Ile Pro Ile Asn Ile Arg Gly Gln Ile Asp
        915                 920                 925
Arg Ile Asp Thr Tyr Thr Lys Asn Asp Thr Ser Phe Val Asn Ile Ile
930                 935                 940
Asp Tyr Lys Ser Ser Glu Gly Ser Ala Thr Leu Asp Leu Thr Lys Val
945                 950                 955                 960
Tyr Tyr Gly Met Gln Met Gln Met Thr Tyr Met Asp Ile Val Leu
                965                 970                 975
Gln Asn Lys Gln Arg Leu Gly Leu Thr Asp Ile Val Lys Pro Gly Gly
            980                 985                 990
Leu Leu Tyr Phe His Val His Glu Pro Arg Ile Lys Phe Lys Ser Trp
        995                 1000                1005
Ser Asp Ile Asp Glu Asp Lys Leu Glu Gln Asp Leu Ile Lys Lys
    1010                1015                1020
Phe Lys Leu Ser Gly Leu Val Asn Ala Asp Gln Thr Val Ile Asp
    1025                1030                1035
Ala Leu Asp Ile Arg Leu Glu Pro Lys Phe Thr Ser Asp Ile Val
    1040                1045                1050
Pro Val Gly Leu Asn Lys Asp Gly Ser Leu Ser Lys Arg Gly Ser
    1055                1060                1065
Gln Val Ala Asp Glu Ala Thr Ile Tyr Lys Phe Ile Gln His Asn
    1070                1075                1080
Lys Glu Asn Phe Ile Glu Thr Ala Ser Asn Ile Met Asp Gly His
    1085                1090                1095
Thr Glu Val Ala Pro Leu Lys Tyr Lys Gln Lys Leu Pro Cys Ala
```

| | | | |
|---|---|---|---|
| Phe Cys Ser Tyr Gln Ser Val Cys His Val Asp Gly Met Ile Asp | | | |
| 1115 | 1120 | 1125 | |
| Ser Lys Arg Tyr Arg Thr Val Asp Glu Thr Ile Asn Pro Ile Glu | | | |
| 1130 | 1135 | 1140 | |
| Ala Ile Gln Asn Ile Asn Ile Asn Asp Glu Phe Gly Gly Glu Gln | | | |
| 1145 | 1150 | 1155 | |

<210> SEQ ID NO 10
<211> LENGTH: 3654
<212> TYPE: DNA
<213> ORGANISM: S. aureus

<400> SEQUENCE: 10

```
atgacaattc cagagaaacc acaaggcgtg atttggactg acgcgcaatg gcaaagtatt      60
tacgcaactg acaagatgt acttgttgca gccgcggcag gttcaggtaa acagctgta      120
ctagttgagc gtattatcca aaagatttta cgtgatggca ttgatgtcga tcgacttta      180
gtcgtaacgt ttacaaactt aagcgcacgt gaaatgaagc atcgtgtaga ccaacgtatt      240
caagaggcat cgattgctga tcctgcaaat gcacacttga aaaccaacg catcaaaatt      300
catcaagcac aaatatctac actccatagt ttttgcttga aattaattca acagcattat      360
gatgtattaa atattgaccc gaactttaga caagcagtg aagctgaaaa tatttatta      420
ttagaacaaa cgatagatga ggtcatagaa caacattacg atatccttga tcctgctttt      480
attgaattaa cagagcaatt gtcttcagat agaagtgatg atcagtttcg aatgattatt      540
aaacaattgt atttctttag cgttgcaaat ccaaatccta caattggtt ggatcaattg      600
gtgacaccat acgaagaaga agcacaacaa gcgcaactta tcaactact aacagactta      660
tctaaagtat ttatcacagc tgcttatgat gctttaaata aggcgtatga tttgtttagt      720
atgatggata gcgtcgataa acatttagct gttatagaag atgaacgacg tttaatgggg      780
cgtgttttag aaggtggctt tattgatata ccttatttaa ctggtcacga atttggcgcg      840
cgtttgccta atgtaacagc gaaaattaaa gaagcaaatg aaatgatggt cgatgcctta      900
gaagatgcta aacttcagta taaaaaatat aaatcattaa ttgataaagt gaagagtgat      960
tacttttcaa gagaagctga tgatttgaaa gctgatatgc aacaattggc gccacgagta     1020
aagtaccttg cgcgtattgt gaaagatgtt atgtcagaat tcaatcgaaa aaagcgtagc     1080
aaaaatattt tggatttttc tgattatgaa catttttgcat acaaattttt aactaatgag     1140
gatggttcgc cttcagaaat tgccgaatca taccgtcaac acttccaaga atattggtc     1200
gatgagtatc aagatacgaa ccgagttcaa gagaaaatac tatcttgcat caaaacgggt     1260
gatgaacata atggtaattt atttatggtt ggagatgtta agcaatccat ttataaattt     1320
agacaagctg atccaagttt atttattgaa aagtatcaac gctttactat agatggagat     1380
ggcactggac gtcgaattga tttgtcgcaa aacttccgtt ctcgaaaaga agtactgtca     1440
acgactaact atatattcaa acatatgatg gatgaacaag tcggtgaagt aaaatatgat     1500
gaagcggcac agttgtatta tggtgcacca tatgatgaat cggaccatcc agtaaactta     1560
aaagtccttg ttgaagcgga tcaagaacat agtgatttaa ctggtagtga acaagaagcg     1620
catttttatag tagaacaagt taaagatatc ttagaacatc aaaaagttta tgatatgaaa     1680
acaggaagct atagaagtgc gacatacaag gatatcgtta ttctagaacg cagctttgga     1740
caagctcgca atttacaaca agcctttaaa aatgaagata ttccattcca tgtgaatagt     1800
```

```
cgtgaaggtt actttgaaca acagaagtc cgcttagtat tatcattttt aagagcgata    1860
gataatccat tacaagatat ttatttagtt gggttaatgc gctccgttat atatcagttc    1920
aaagaagacg aattagctca aattagaata ttgagtccaa atgatgacta cttctatcaa    1980
tcgattgtaa attacattaa tgacgaagca gcagatgcaa ttttagttga taaattaaaa    2040
atgttttat cagatattca aagttaccaa caatatagta aagatcatcc ggtgtatcag    2100
ttaattgata aattttataa tgatcattat gttattcaat actttagtgg acttattggt    2160
ggacgtggac gacgtgcaaa tctttatggt ttatttaata aagctatcga gtttgagaat    2220
tcaagtttta gaggtttata tcaatttatt cgttttatcg atgaattgat tgaaagaggc    2280
aaagattttg gtgaggaaaa atgtagttgg tccaaacgata atgtcgttag aatgatgaca    2340
attcatagta gtaaaggtct agagtttcca tttgtcattt attctggatt gtcaaaagat    2400
tttaataaac gtgatttgaa acaaccagtt attttaaatc agcaatttgg tctcggaatg    2460
gattattttg atgtggataa agaaatggca tttccatctt tagcttcggt tgcatataga    2520
gctgttgccg aaaagaaact tgtgtcagaa gaaatgcgat tagtctatgt agcattaaca    2580
agagcgaaag aacaacttta tttaattggt agagtgaaaa atgataaatc attactagaa    2640
ctagagcaat tgtctatttc tggtgagcac attgctgtca atgaacgatt aacttccacca    2700
aatccgttcc atcttatttta tagtatttta tctaaacatc aatctgcgtc aattccagat    2760
gatttaaaat ttgaaaaaga tatagcacaa attgaagata gtagtcgtcc gaatgtaaat    2820
atttcaattg tgtactttga agatgtgtct acagaaacca ttttagataa tgatgaatat    2880
cgttcggtta tcaattaga aactatgcaa atggtaatg aagatgttaa agcacaaatt    2940
aaacaccaac ttgattatcg atatccatat gtaaatgata ctaaaaagcc ctcaaaacaa    3000
tctgtttctg aattgaaaag acaatatgaa acagaagaaa gtggcacaag ttacgaacga    3060
gtaaggcaat atcgtatcgg ttttcaacg tatgaacgac ctaaatttct aagtgaacaa    3120
ggtaaacgaa aagcgaatga aattggtacg ttaatgcata cagtgatgca acatttacca    3180
ttcaaaaaag aacgcatatc tgaagttgag ttacatcagt atatcgatgg attaatcgat    3240
aaacatatta tcgaagcaga tgcgaaaaaa gatatccgta tggatgaaat aatgacattt    3300
atcaatagtg agttatattc gattattgct gaagcagagc aagtttatcg tgaattaccg    3360
tttgtagtta accaagcatt agttgaccaa ttgccacaag gagacgaaga cgtctcaatt    3420
attcaaggta tgattgactt aatctttgtt aaagatggtg tgcattattt tgtagactat    3480
aaaaccgatg catttaatcg tcgccgtggg atgacagatg aagaaattgg tacacaatta    3540
aaaaataaat ataagataca gatgaaatat tatcaaaata cgcttcaaac gattcttaat    3600
aaagaagtta aaggttattt atacttcttc aaatttggta cattgcaact atag            3654
```

<210> SEQ ID NO 11
<211> LENGTH: 1217
<212> TYPE: PRT
<213> ORGANISM: S. aureus

<400> SEQUENCE: 11

```
Met Thr Ile Pro Glu Lys Pro Gln Gly Val Ile Trp Thr Asp Ala Gln
1               5                   10                  15

Trp Gln Ser Ile Tyr Ala Thr Gly Gln Asp Val Leu Val Ala Ala Ala
            20                  25                  30

Ala Gly Ser Gly Lys Thr Ala Val Leu Val Glu Arg Ile Ile Gln Lys
        35                  40                  45
```

-continued

```
Ile Leu Arg Asp Gly Ile Asp Val Asp Arg Leu Leu Val Val Thr Phe
    50                  55                  60

Thr Asn Leu Ser Ala Arg Glu Met Lys His Arg Val Asp Gln Arg Ile
65                  70                  75                  80

Gln Glu Ala Ser Ile Ala Asp Pro Ala Asn Ala His Leu Lys Asn Gln
                85                  90                  95

Arg Ile Lys Ile His Gln Ala Gln Ile Ser Thr Leu His Ser Phe Cys
            100                 105                 110

Leu Lys Leu Ile Gln Gln His Tyr Asp Val Leu Asn Ile Asp Pro Asn
        115                 120                 125

Phe Arg Thr Ser Ser Glu Ala Glu Asn Ile Leu Leu Leu Glu Gln Thr
130                 135                 140

Ile Asp Glu Val Ile Glu Gln His Tyr Asp Ile Leu Asp Pro Ala Phe
145                 150                 155                 160

Ile Glu Leu Thr Glu Gln Leu Ser Ser Asp Arg Ser Asp Asp Gln Phe
                165                 170                 175

Arg Met Ile Ile Lys Gln Leu Tyr Phe Phe Ser Val Ala Asn Pro Asn
            180                 185                 190

Pro Thr Asn Trp Leu Asp Gln Leu Val Thr Pro Tyr Glu Glu Glu Ala
        195                 200                 205

Gln Gln Ala Gln Leu Ile Gln Leu Leu Thr Asp Leu Ser Lys Val Phe
210                 215                 220

Ile Thr Ala Ala Tyr Asp Ala Leu Asn Lys Ala Tyr Asp Leu Phe Ser
225                 230                 235                 240

Met Met Asp Ser Val Asp Lys His Leu Ala Val Ile Glu Asp Glu Arg
                245                 250                 255

Arg Leu Met Gly Arg Val Leu Glu Gly Gly Phe Ile Asp Ile Pro Tyr
            260                 265                 270

Leu Thr Gly His Glu Phe Gly Ala Arg Leu Pro Asn Val Thr Ala Lys
        275                 280                 285

Ile Lys Glu Ala Asn Glu Met Met Val Asp Ala Leu Glu Asp Ala Lys
290                 295                 300

Leu Gln Tyr Lys Lys Tyr Lys Ser Leu Ile Asp Lys Val Lys Ser Asp
305                 310                 315                 320

Tyr Phe Ser Arg Glu Ala Asp Asp Leu Lys Ala Asp Met Gln Gln Leu
                325                 330                 335

Ala Pro Arg Val Lys Tyr Leu Ala Arg Ile Val Lys Asp Val Met Ser
            340                 345                 350

Glu Phe Asn Arg Lys Lys Arg Ser Lys Asn Ile Leu Asp Phe Ser Asp
        355                 360                 365

Tyr Glu His Phe Ala Leu Gln Ile Leu Thr Asn Glu Asp Gly Ser Pro
370                 375                 380

Ser Glu Ile Ala Glu Ser Tyr Arg Gln His Phe Gln Glu Ile Leu Val
385                 390                 395                 400

Asp Glu Tyr Gln Asp Thr Asn Arg Val Gln Glu Lys Ile Leu Ser Cys
                405                 410                 415

Ile Lys Thr Gly Asp Glu His Asn Gly Asn Leu Phe Met Val Gly Asp
            420                 425                 430

Val Lys Gln Ser Ile Tyr Lys Phe Arg Gln Ala Asp Pro Ser Leu Phe
        435                 440                 445

Ile Glu Lys Tyr Gln Arg Phe Thr Ile Asp Gly Asp Gly Thr Gly Arg
450                 455                 460

Arg Ile Asp Leu Ser Gln Asn Phe Arg Ser Arg Lys Glu Val Leu Ser
```

```
            465                 470                 475                 480
Thr Thr Asn Tyr Ile Phe Lys His Met Met Asp Glu Gln Val Gly Glu
                    485                 490                 495
Val Lys Tyr Asp Glu Ala Ala Gln Leu Tyr Tyr Gly Ala Pro Tyr Asp
                500                 505                 510
Glu Ser Asp His Pro Val Asn Leu Lys Val Leu Val Glu Ala Asp Gln
                515                 520                 525
Glu His Ser Asp Leu Thr Gly Ser Glu Gln Glu Ala His Phe Ile Val
            530                 535                 540
Glu Gln Val Lys Asp Ile Leu Glu His Gln Lys Val Tyr Asp Met Lys
545                 550                 555                 560
Thr Gly Ser Tyr Arg Ser Ala Thr Tyr Lys Asp Ile Val Ile Leu Glu
                565                 570                 575
Arg Ser Phe Gly Gln Ala Arg Asn Leu Gln Gln Ala Phe Lys Asn Glu
                580                 585                 590
Asp Ile Pro Phe His Val Asn Ser Arg Glu Gly Tyr Phe Glu Gln Thr
                595                 600                 605
Glu Val Arg Leu Val Leu Ser Phe Leu Arg Ala Ile Asp Asn Pro Leu
            610                 615                 620
Gln Asp Ile Tyr Leu Val Gly Leu Met Arg Ser Val Ile Tyr Gln Phe
625                 630                 635                 640
Lys Glu Asp Glu Leu Ala Gln Ile Arg Ile Leu Ser Pro Asn Asp Asp
                645                 650                 655
Tyr Phe Tyr Gln Ser Ile Val Asn Tyr Ile Asn Asp Glu Ala Ala Asp
                660                 665                 670
Ala Ile Leu Val Asp Lys Leu Lys Met Phe Leu Ser Asp Ile Gln Ser
            675                 680                 685
Tyr Gln Gln Tyr Ser Lys Asp His Pro Val Tyr Gln Leu Ile Asp Lys
            690                 695                 700
Phe Tyr Asn Asp His Tyr Val Ile Gln Tyr Phe Ser Gly Leu Ile Gly
705                 710                 715                 720
Gly Arg Gly Arg Arg Ala Asn Leu Tyr Gly Leu Phe Asn Lys Ala Ile
                725                 730                 735
Glu Phe Glu Asn Ser Ser Phe Arg Gly Leu Tyr Gln Phe Ile Arg Phe
                740                 745                 750
Ile Asp Glu Leu Ile Glu Arg Gly Lys Asp Phe Gly Glu Glu Asn Val
                755                 760                 765
Val Gly Pro Asn Asp Asn Val Val Arg Met Met Thr Ile His Ser Ser
770                 775                 780
Lys Gly Leu Glu Phe Pro Phe Val Ile Tyr Ser Gly Leu Ser Lys Asp
785                 790                 795                 800
Phe Asn Lys Arg Asp Leu Lys Gln Pro Val Ile Leu Asn Gln Gln Phe
                805                 810                 815
Gly Leu Gly Met Asp Tyr Phe Asp Val Asp Lys Glu Met Ala Phe Pro
                820                 825                 830
Ser Leu Ala Ser Val Ala Tyr Arg Ala Val Ala Glu Lys Glu Leu Val
            835                 840                 845
Ser Glu Glu Met Arg Leu Val Tyr Val Ala Leu Thr Arg Ala Lys Glu
                850                 855                 860
Gln Leu Tyr Leu Ile Gly Arg Val Lys Asn Asp Lys Ser Leu Leu Glu
865                 870                 875                 880
Leu Glu Gln Leu Ser Ile Ser Gly Glu His Ile Ala Val Asn Glu Arg
            885                 890                 895
```

-continued

```
Leu Thr Ser Pro Asn Pro Phe His Leu Ile Tyr Ser Ile Leu Ser Lys
            900                 905                 910

His Gln Ser Ala Ser Ile Pro Asp Asp Leu Lys Phe Glu Lys Asp Ile
            915                 920                 925

Ala Gln Ile Glu Asp Ser Ser Arg Pro Asn Val Asn Ile Ser Ile Val
930                 935                 940

Tyr Phe Glu Asp Val Ser Thr Glu Thr Ile Leu Asp Asn Asp Glu Tyr
945                 950                 955                 960

Arg Ser Val Asn Gln Leu Glu Thr Met Gln Asn Gly Asn Glu Asp Val
            965                 970                 975

Lys Ala Gln Ile Lys His Gln Leu Asp Tyr Arg Tyr Pro Tyr Val Asn
            980                 985                 990

Asp Thr Lys Lys Pro Ser Lys Gln Ser Val Ser Glu Leu Lys Arg Gln
            995                 1000                1005

Tyr Glu Thr Glu Glu Ser Gly Thr Ser Tyr Glu Arg Val Arg Gln
    1010                1015                1020

Tyr Arg Ile Gly Phe Ser Thr Tyr Glu Arg Pro Lys Phe Leu Ser
    1025                1030                1035

Glu Gln Gly Lys Arg Lys Ala Asn Glu Ile Gly Thr Leu Met His
    1040                1045                1050

Thr Val Met Gln His Leu Pro Phe Lys Lys Glu Arg Ile Ser Glu
    1055                1060                1065

Val Glu Leu His Gln Tyr Ile Asp Gly Leu Ile Asp Lys His Ile
    1070                1075                1080

Ile Glu Ala Asp Ala Lys Lys Asp Ile Arg Met Asp Glu Ile Met
    1085                1090                1095

Thr Phe Ile Asn Ser Glu Leu Tyr Ser Ile Ile Ala Glu Ala Glu
    1100                1105                1110

Gln Val Tyr Arg Glu Leu Pro Phe Val Val Asn Gln Ala Leu Val
    1115                1120                1125

Asp Gln Leu Pro Gln Gly Asp Glu Asp Val Ser Ile Ile Gln Gly
    1130                1135                1140

Met Ile Asp Leu Ile Phe Val Lys Asp Gly Val His Tyr Phe Val
    1145                1150                1155

Asp Tyr Lys Thr Asp Ala Phe Asn Arg Arg Arg Gly Met Thr Asp
    1160                1165                1170

Glu Glu Ile Gly Thr Gln Leu Lys Asn Lys Tyr Lys Ile Gln Met
    1175                1180                1185

Lys Tyr Tyr Gln Asn Thr Leu Gln Thr Ile Leu Asn Lys Glu Val
    1190                1195                1200

Lys Gly Tyr Leu Tyr Phe Phe Lys Phe Gly Thr Leu Gln Leu
    1205                1210                1215
```

ENHANCEMENT OF CRISPR GENE EDITING OR TARGET DESTRUCTION BY CO-EXPRESSION OF HETEROLOGOUS DNA REPAIR PROTEIN

CROSS REFERENCE TO RELATED APPLICATIONS

This application claims priority to U.S. provisional patent application No. 62/516,634, filed Jun. 7, 2017, the disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 6, 2018, is named RexAB_Sequence_listing_PCT.txt and is 90,811 bytes in size.

FIELD OF THE DISCLOSURE

The present disclosure is related to compositions and methods for improving CRISPR target editing.

BACKGROUND OF THE DISCLOSURE

Some type II clustered regularly interspaced short palindromic repeats (CRISPR) CRISPR-Cas systems encode a single gene, cas9, which can cleave DNA targets complementary to an RNA guide. For conventional Cas9 targeting, and when heterologously expressed in mammalian cells with a DNA template for homology-directed repair, Cas9 cleavage can mediate rapid and customizable genome editing. The easy programmability of this breakthrough editing technology has led to the creation of several large companies, and clinical trials for Cas9-editing therapies for several genetic diseases are underway. However, editing efficiencies remain sub-optimal and off-target effects could be a major obstacle for the further development of Cas9 therapies in humans. There is thus an ongoing and unmet need for improvements in CRISPR-Cas targeting and editing. The present disclosure is pertinent to this need.

SUMMARY

The present disclosure provides compositions, methods, and kits for improving CRISPR-based editing of DNA targets by a CRISPR-associated (Cas) enzyme, such as a Cas9 enzyme, by combining the Cas enzyme and a suitable CRISPR targeting RNA, such as a guide RNA (gRNA), with a heterologous DNA repair enzyme. In embodiments, the heterologous DNA repair enzyme is one of RecBCD, AddAB, or AdnAB. In certain embodiments, such as for use in eukaryotic cells, the RecBC, AddAB, or AdnAB has inactivated nuclease activity. The proteins and targeting RNA, along with, if desired, a DNA repair template that can be involved in DNA editing, can be introduced into cells using any suitable approaches, including but not necessarily limited to using one or more expression vectors, such as plasmids. In certain embodiments, editing of the DNA is enhanced relative to a control value obtained or derived from DNA editing in the absence of the heterologous RecBCD, AddAB, or AdnAB. In certain approaches the disclosure includes providing a DNA repair template, of which all or a segment is introduced into DNA in the cell. The DNA in the cell that is modified can be a chromosome, or an episomal element, such as a plasmid. In certain implementations, the DNA repair template comprises at least one mutation that is introduced into the DNA in the cell. The mutation can be any desired mutation, and may result in a modified segment of DNA in the cell that has from a single nucleotide change, such as an insertion or deletion, to changes, additions, or deletions of many more nucleotides, limited only by the DNA repair template that is provided to the cell as a component of a CRISPR system of this disclosure. In a non-limiting example, the mutation comprises a CRISPR-blocking mutation, which prevents successive rounds of cleavage by the CRISPR system. In certain examples, the heterologous RecBCD, AddAB, or AdnAB has inactivated nuclease activity.

The disclosure includes cells that comprise some or all of the CRISPR system components described herein, cells that comprise genetic modifications using such CRISPR systems, progeny of the cells, non-human animals made from or into which the modified cells are introduced, and products made by the cells. The modified cells may be used for any purpose, such as industrial purposes in the case of prokaryotes and fungi, or for human or veterinary therapeutic purposes. Cells that can be modified using embodiments of the disclosure are not particularly limited to any cell types, and thus can any bacteria, including Gram positive and Gram negative bacteria, or plant, animal, fungal, or protozoan cells.

The disclosure also provides kits for making genetic modifications as described herein. In embodiments, a kit comprises one or more vectors, such as plasmids, but any other expression vector can be used, wherein the one or more vectors encode a CRISPR Cas enzyme, and at least one of RecBC, AddAB, or AdnAB. In embodiments, the expression vector provided with a kit encodes RecBC, AddAB, or AdnAB that has inactivated nuclease activity. The kits may further comprise other components, such one or more buffers, primers, restriction enzymes, reagents for introducing the expression vectors into cells, or printed material, such as labeling or instructions on using the kit components.

BRIEF DESCRIPTION OF THE FIGURES

FIG. 1. Graphs demonstrating that AddAB enhances Cas9 phage interference in *S. aureus*. *S. aureus* wild type (black) or addA″ (gray) cells harboring an empty plasmid (pC194, dotted line) or a plasmid expressing the *S. pyogenes* CRISPR-Cas system programmed with an early (dotted-dashed line) or late (full line) target against the phage φNM4y4 were treated without phage (left panel) or with φNM4y4 at a multiplicity of infection (MOI) of 280 (right panel). addA″ cells suffer a significant growth defect for both early and late targets indicating that the nuclease activity of AddA is required for complete Cas9 targeting and phage clearance in prokaryotic cells.

FIG. 2. Images showing SaAddAB enhances Cas9 targeting of λ in *E. coli*. To obtain the data shown in FIG. 2, *E. coli* cells harboring plasmid pCL120 (empty) or pCL1920 expressing one of five different phage λ spacers were suspended in to LB agar and treated with 10-fold dilutions of λ. For all spacers tested, the co-expression of SaAddAB enhanced λ clearance by 10-1000×. SaAddAB expression did not affect λ viability in the absence of Cas9 targeting, indicating that SaAddAB specifically enhances Cas9 interference of phage targets, which indicates enhanced Cas9 activity.

FIG. 3. SaAddAB and Cas9 interact in a bacterial two-hybrid system. *E. coli* BTH101 cells co-expressing N- and C-terminal fusions of T25 to Cas9 and T118 to SaAddA, SaAddB or SaAddAB were spotted on MacConkey agar plates supplemented with maltose. Darker spots indicate a positive interaction while lighter spots indicate a negative interaction. Negative and positive control spots are shown in the bottom panel. The results show that SaAddAB and Cas9 interact, indicating that SaAddAB enhances Cas9 activity.

Figure 4:
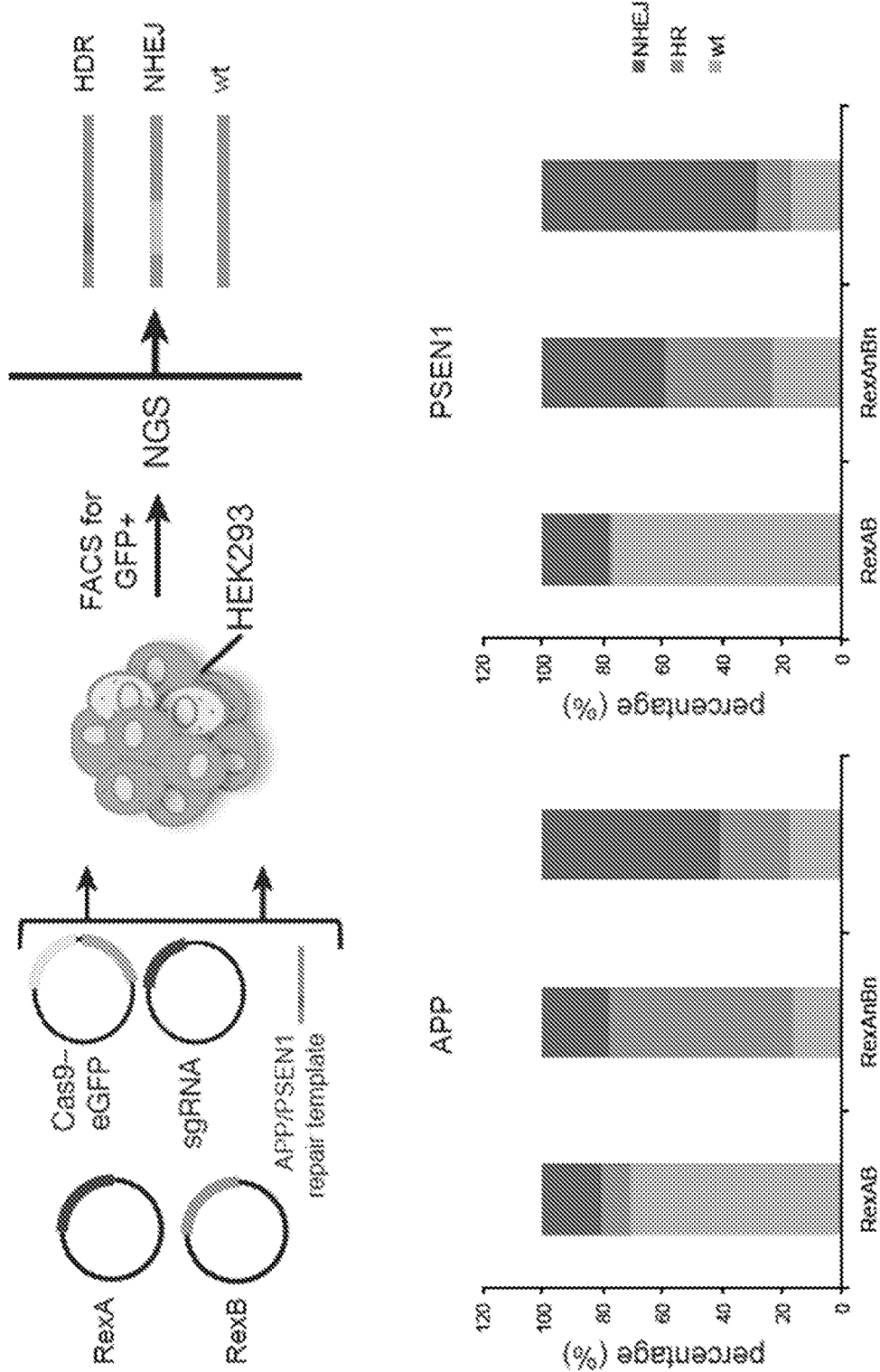

FIG. 4. Nuclease-dead RexA and RexB co-expression improves CRISPR/Cas9-mediated homology-directed repair (HDR) in human cells. HEK293 cells were transfected with plasmids containing Cas9_2A_GFP, sgRNAs targeting the human APP or PSEN1 gene, repair single-stranded oligodeoxynucleotides (ssODNs) to introduce mutations into APP or PSEN1, and plasmids encoding human codon-optimized RexA and RexB. Green fluorescent protein (GFP)-positive cells were isolated by fluorescence activated cell sorting and their genomes analyzed for editing of the APP or PSEN1 locus for HDR or non-homologous end-joining (NHEJ). While HEK293 cells transfected with RexA and RexB show decreased HDR, cells transfected with nuclease-dead versions of RexA and RexB show enhanced HDR, in comparison to cells not transfected with Rex constructs. For this figure, Cas9 and AddAB are from S. *Pyogenes*.

DETAILED DESCRIPTION OF THE DISCLOSURE

Unless defined otherwise herein, all technical and scientific terms used herein have the same meaning as commonly understood by one of ordinary skill in the art to which this disclosure pertains. As used herein, RexA and AddA are synonyms; RexB and AddB are synonyms; and RexAB and AddAB are synonyms.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All nucleotide sequences described herein include the RNA and DNA equivalents of such sequences, i.e., an RNA sequence includes its cDNA. All nucleotide sequences include their complementary sequences.

All nucleotide and amino sequences identified by reference to a database, such as a GenBank database reference number, are incorporated herein by reference as the sequence exists on the filing date of this application or patent.

Any component of the editing systems described herein can be provided on the same or different polynucleotides, such as plasmids, or a polynucleotide integrated into a chromosome. In embodiments, a component of the system is heterologous to the cells. In embodiments, any enzyme or other protein as described herein is introduced into the cell as a recombinant or purified protein, or as an RNA encoding the enzyme that is expressed once introduced into the cell, or as an expression vector, which is expressed once in the cell. Any suitable expression system can be used and many are commercially available for use with the instant invention, given the benefit of the present description.

In embodiments the present disclosure provides compositions and methods for improving the specificity, efficiency, or other desirable properties of CRISPR-based gene editing or target destruction in any cell or organism of interest. In various embodiments, the disclosure includes a bacterial CRISPR (clustered regularly interspaced short palindromic repeats)/Cas (CRISPR-associated protein). In embodiments, a CRISPR-Cas enzyme that is a Type II Cas enzyme is used. Many suitable such Cas amino acid sequences are known in the art, and expression vectors encoding such Cas enzymes are commercially available. In embodiments, a CRISPR Cas enzyme used herein is a Cas9 enzyme having the amino acid sequence, or a derivative thereof, of the Cas9 encoded by *Streptococcus pyogenes*. In embodiments, CRISPR enzyme is CRISPR enzyme that is distinct from *S. pyogenes* Cas9. In embodiments, the Cas enzyme is a *Staph. aureus* Cas9.

In embodiments, the disclosure provided for increased DNA editing, relative to a control value. In embodiments, the disclosure provides for increased editing that involves homology-directed repair (HDR), as compared to non-homologous end joining (NHEJ). In this regard, it is known in the art that a CRISPR gRNA targets a Cas9 to a specific genomic locus by RNA-DNA base pairing adjacent to a protospacer adjacent motif (PAM) on the DNA. In embodiments, the PAM is NGG, such as for CRISPR systems that involve *S. pyogenes* Cas9. Those skilled in the art will be understand that other PAM sequences may be recognizes by Cas enzymes from different bacterial types. Nevertheless, both the presence of a PAM and gRNA binding are required for Cas9 to introduce a site-specific double-strand break (DSB), which occurs 3 bp upstream of the PAM motif. The CRISPR/Cas9 complex has been shown to be very efficient at introducing DSBs in the DNA of many cell types and model systems. In most cases these DSBs are repaired by the NHEJ pathway, whereas in some cases the cellular repair mechanism can utilize another DNA molecule, such as an externally introduced DNA template, to repair the chromosome break by HR. Introducing a modified donor template, such as a single-stranded oligo DNA nucleotide (ssODN) repair template, can yield intended base changes. The present disclosure facilitates precise editing by HDR to engineer specific mutations, as described further below. In embodiments, the disclosure provides for increased HDR to incorporate all or a segment of a DNA repair template, relative to editing that occurs by NHEJ. In embodiments, the increased editing is greater than a control value, such as editing in cells that comprise a CRISPR-based DNA editing system, but do not include a heterologous DNA repair enzyme, as further described below. The control value can be any value based on, for example, DNA editing in the absence of any one or combination of RecBCD, AddAB, or AdnAB, or proteins with similar activities. Those skilled in the art can readily determining if an editing event was cause by HDR or NHEJ, such as by sequencing the segment of DNA that was edited.

"Heterologous" means that the cells into which the one or more heterologous Cas and/or DNA repair enzymes are introduced do not have polynucleotide sequences encoding the one or more heterologous DNA repair enzymes, or the Cas enzyme, respectively, prior to such cells being modified as described herein. Methods of making the modified cells are included, as are methods comprising modifying cells by engineering the cells such that they express a heterologous DNA repair enzyme, and/or a heterologous a Cas enzyme, and and/or a heterologous guide RNA (gRNA), are included. As is known in the art, gRNAs are generally short RNA polynucleotides that comprise a sequence necessary for Cas-binding, and an approximately 20 nucleotide spacer that defines a DNA target that is edited using the CRISPR system. Use of more than one guide RNA can also be included. Methods for making gRNAs targeted to any particular sequence that is susceptible to CRISPR editing are well known in the art. The disclosure also comprises optionally using other polynucleotides, such as any suitable activating crRNA (tracrRNA), which comprises a segment that is complementary to a pre-crRNA, such that a portion of the tracrRNA and pre-crRNA can form an RNA duplex that is modified to participate in CRISPR editing. In embodiments, a fusion of crRNA and tracrRNA (a sgRNA) is used, which provides for targeting and binding to, for example, a Cas9.

Additional polynucleotides can be introduced for purposes such as creating a mutation, an insertion, or a deletion of a segment of DNA in the cells, as described further below.

The disclosure comprises the modified cells, methods of making the cells, and cells that are mutated using the compositions and methods of this disclosure, and progeny of such cells, including but not limited to modified organisms which include and/or develop from such cells.

In embodiments, the disclosure uses DNA repair enzymes that are heterologous enzyme(s) that are bacterial end-repair complexes. In embodiments, the DNA repair enzymes comprise RecBCD, AddAB, or AdnAB, or fragments thereof, provided the fragments can participate in DNA editing as described herein. In optional embodiments, the RecBCD, AddAB, or AdnAB or fragments thereof have inactivated nuclease activity, as described further below. addAB/rexAB proteins are referred to herein from time to time and for convenience as AddAB.

In non-limiting embodiments the heterologous DNA repair enzyme is from, or is a derivative, of a DNA repair enzyme from any strain or species or subspecies of bacteria. In embodiments, the heterologous DNA repair enzyme is from a *Staphylococcus*. In embodiments the heterologous DNA repair enzyme is from *S. aureus* or *S. pyogenes*. In embodiments, the heterologous DNA repair enzyme is from *E. coli*. In embodiments, the heterologous DNA repair enzyme is from *B. subtilis*. In embodiments, the heterologous DNA repair enzyme is from *M. smegmatis*. In embodiments, the heterologous DNA repair enzyme comprises any homologue or derivative of DNA repair enzyme from the foregoing types of bacteria, provided the DNA repair enzyme can function in DNA editing as described herein.

In embodiments the Cas amino acid sequence, and/or the heterologous DNA repair enzymes amino acid sequence, has between 50-100% identity to a wild type amino acid sequence. In embodiments, the Cas amino acid sequence and/or the heterologous DNA repair enzyme amino acid sequence comprises a truncation and/or deletion such that only a segment of the protein that is required to achieve a desired effect (i.e., an improvement in Cas editing relative to a reference) is achieved. In embodiments, the Cas amino acid sequence and/or the heterologous DNA repair enzyme amino acid sequence includes additional amino acids at the N- or C-terminus, relative to a wild type sequence. In embodiments the disclosure includes cells modified such that they express only one of a heterologous DNA repair enzyme, in addition to the Cas and other genetic elements as described herein. In embodiments, modified cells of this disclosure comprise a complex of Cas and one or more heterologous DNA repair enzymes. In embodiments the Cas can be obtained and/or derived from any bacteria that produces a Cas enzyme. In certain embodiments the Cas is a Cas9 obtained and/or derived from *Streptococcus, Staphylococcus*, or *Neisseria*. In one embodiment, the Cas is a Cas9 having a Cas9 amino acid sequence encoded by *Streptococcus pyogenes*. In one embodiment, the Cas9 is a variant Cas9 that comprises one or more mutations.

In embodiments, the DNA repair enzymes and/or a Cas enzyme have an amino acid sequence described herein, and/or are encoded by any of the nucleotide sequences described herein, or any sequence having at least from 50%-100%, inclusive, and including all integers and ranges of integers there between, identity with the foregoing nucleotide and/or amino acid sequences. In embodiments, the sequences used in this disclosure have 90, 91, 92, 93, 94, 95, 96, 97, 98, or 99% identity across the entire length or a functional segment thereof of the sequences described herein. Thus, variants of the Cas proteins and DNA repair enzyme proteins and their nucleotide sequences are included. The term "variant" and its various grammatical forms as used herein refers to a nucleotide sequence or an amino acid sequence with substantial identity to a reference nucleotide sequence or reference amino acid sequence, respectively. The differences in the sequences may be the result of changes, either naturally or by design, in sequence or structure. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

In more detail, in embodiments, a heterologous DNA repair enzyme used in the disclosure may comprise one or more mutations that reduce or eliminate the function of a nuclease activity of the protein(s). In embodiments, the nuclease activity is eliminated, such that no detectable nuclease activity is observed when the protein(s) contact a polynucleotide substrate. In embodiments, the degree of nuclease activity may be determined by mixing a DNA repair enzyme with a test template DNA and determining nuclease activity (or lack thereof) by sequencing the template DNA or by gel electrophoresis and/or PCR amplification of the test template subsequent to exposing the test template to the DNA repair enzyme. In embodiments, a mutation inhibits and/or prevents formation of an enzyme complex, wherein the complex comprises nuclease activity. In embodiments, a mutation that affects nuclease activity comprises one or more amino acid changes in the DNA repair enzyme, which may comprise a single amino acid change, or a truncation or other disruption of a nuclease domain and/or nuclease active site.

In embodiments, the disclosure includes the following representative DNA repair enzyme sequences (which provide non-limiting reference amino acid positions of certain non-limiting mutations, such as nuclease inactivating mutations):

RecB (GenBank accession no: NP 417297.1; *E. coli* K-12);
RecC (GenBank accession no NP_417299; *E. coli* K-12);
AddA (GenBank accession no. NP_388944.2; *B. subtilis*);
AddB (GenBank accession no. NP_388943.2; *B. subtilis*);
RexA (GenBank accession no. AIL10952.1; *S. pyogenes*);
AddB (GenBank accession no. AMY97143.1; *S. pyogenes*);
AdnA (GenBank accession no. YP_886307.1; *M. smegmatis*); and AdnB (GenBank accession no. YP_886308.1; *M. smegmatis*). Thus, in embodiments, the disclosure includes wild-type and nuclease-dead mutants of bacterial DNA repair enzyme.

In non-limiting embodiments, the disclosure includes DNA repair enzymes that comprise any one or combinations of the following mutations:

RecBCD family mutants: Representative mutants for this family are based on the *E. coli* K-12 genes, but any homologous proteins can be included, and similar amino acid mutations can be made in the homologous proteins. In embodiments, the disclosure includes mutants that prevent RecD from associating with RecBC. Mutation amino acid locations are designated in conjunction with the GenBank sequences described above, and include, for example, recC (G905E), or a C-terminal RecC truncation starting at amino acid residues 678 through 1084, or a deletion of recD (ArecD). Mutations that decrease and/or eliminate nuclease activity include but are not necessarily limited to mutations in the RecB nuclease domain: RecB (D1067A), RecB (D1080A), RecB (K1082A), and mutations in RecB conserved residues in its Ca-binding domain: H956A, E1020A.

AddAB family nuclease-dead mutants: Mutation amino acid locations are designated in conjunction with the GenBank sequences described above, and include, for example, mutations in the AddA and AddB nuclease domains (positions from *B. subtilis* genes; homologous genes/mutations from other bacteria types are included): AddA (D1159A); AddA (D1172A); AddA (K1174A); AddB (NP_388943.2); AddB (D947A); AddB (D961A); AddB (K963A).

RexA and RexB nuclease domain mutation positions from *S. pyogenes* genes (homologous genes/mutations from other bacteria types are included). Mutation amino acid locations are designated in conjunction with the GenBank sequences described above, and include, for example: RexA (D1144A); RexA (D1157A); RexA (K1159A); AddB (AMY97143.1); RexB (D874A); RexB (D888A); RexB (K890A), and a RexA (D1157A) RexB (D888A) double mutant.

AdnAB family nuclease-dead mutants: (positions from *M. smegmatis* genes, homologous genes/mutations from other bacteria types are included): Mutation amino acid locations are designated in conjunction with the GenBank sequences described above, and include, for example: AdnA (YP_886307.1); AdnA (H833A); AdnA (D920A); AdnA (D934A); AdnA (K936A); AdnB (YP_886308.1); AdnB (H928A); AdnB (D992A); AdnB (D1007A); and AdnB (K1009A).

Additional representative sequences are encompassed by this disclosure, and include, for example, plasmid sequences, inactivated nuclease sequences, and gRNAs. The plasmids include pCS2+_EF1a_RexA_3xFLAG_NLS, which encodes a the human codon optimized *S. pyogenes* rexA gene fused at its C-terminus to a 3xFLAG tag and nucleoplasmin NLS tag and driven by the EF1a promoter, and pCS2+_EF1a_RexB_HA_NLS, which is a human codon optimized *S. pyogenes* rexB gene fused at its C-terminus to the HA tag and nucleoplasmin NLS tag, also driven by an EF1a promoter.

Representative and non-limiting sequences are provided by the accompanying sequence listing, in which: SEQ ID NO:1 provides the sequence of the MLM3636_APP-gRNA plasmid sequence. An APP targeting gRNA sequence in DNA form is provided at nucleotides 331 . . . 350; SEQ ID NO:2 provides the MLM3636_PSEN1-gR plasmid sequence. A PSEN1 targeting gRNA sequence in DNA form is provided at nucleotides 331 . . . 349; SEQ ID NO:3 provides the pCas9_2A_GFP plasmid sequence; SEQ ID NO:4 provides the pCS2+_EF1a_RexA_3xFLAG_NLS plasmid sequence; SEQ ID NO:5 provides the pCS2+_EF1a_RexA_ND_3xFLAG_NLS plasmid sequence; SEQ ID NO:6 provides the pCS2+_EF1a_RexB_HA_NLS plasmid sequence; SEQ ID NO:7 provides the pCS2+_EF1a_RexB_ND_HA_NLS plasmid sequence; SEQ ID NO:8 provides a *S. aureus* addB nucleotide coding sequence; SEQ ID NO:9 provides a *S. aureus* addB protein sequence; SEQ ID NO:10 provides a *S. aureus* addA nucleotide coding sequence; and SEQ ID NO:11 provides a *S. aureus* addA protein sequence. The nucleotide sequences that are described in the accompanying sequence listing can be readily translated using a variety of publically available software programs to generate the protein sequences that are encoded by the plasmids, which are encompassed in this disclosure. Promoters and other genetic elements can also be identified and are also included in this description.

A "targeting RNA" is an RNA that, when transcribed from the portion of the CRISPR system encoding it, comprises at least a segment of RNA sequence that is identical to (with the exception of replacing T for U in the case of RNA) or complementary to (and thus "targets") a DNA sequence in a cell into which the system is introduced. In embodiments the targeting RNA is complementary to a sequence in a chromosome or plasmid. The targeting RNA can be directed to a DNA target is in a prokaryotic or eukaryotic cell. The targeting RNA encoded by the CRISPR system can be a CRISPR RNA (crRNA) or a guide RNA, or any other suitable RNA polynucleotide that can participate in directing the Cas, such as a Cas9 to a particular site. The sequence of the targeting RNA is not particularly limited, other than by the requirement for it to be directed to (i.e., having a segment that is the same as or complementary to) a CRISPR site that is specific for a target in the cell(s) wherein a modification is to be made. In embodiments wherein a crRNA is used, including but not necessarily limited to a pre-crRNA, a system of this disclosure may also encode a tracrRNA. In various embodiments, the tracrRNA can comprise a segment that is complementary to a pre-crRNA, such that a portion of the tracrRNA and pre-crRNA can form an RNA duplex. The RNA duplex is cleaved by RNase resulting in the formation of a crRNA/tracrRNA hybrid complex. This hybrid functions as a guide for Cas, which cleaves the target sequence in the bacteria.

There are a wide variety of publicly available resources that can be used to design suitable targeting RNAs that can be adapted for use with embodiments of the present disclosure. In embodiments, the targeting RNA comprises a guide RNA ("gRNA").

In embodiments a polynucleotide comprising or consisting of a targeting RNA can be encoded by the same expression vector that also encodes the Cas9 protein, or the DNA repair enzyme, or it can be expressed from a distinct vector, or it can be introduced into cells directly as an RNA molecule.

In embodiments, the modification of genetic content in a cell using an improved CRISPR-Cas system described herein is improved relative to a reference. Improvement of the modification can include but is not necessarily limited to improved specificity for a target, and/or improved target editing efficiency. In embodiments, the reference is a value determined from using a Cas9 enzyme-based CRISPR editing system in a cell or population of the cells, wherein the cell(s) do not comprise AddAB proteins.

In embodiments the disclosure comprises modifying a cell or a population of cells by introducing into the cells one or a combination of expression vectors or other polynucleotides encoding: i) a Cas9 enzyme; and ii) DNA repair enzyme proteins. In embodiments the disclosure further comprises introducing into such cells a targeting RNA such that genetic content in the cells is modified by the Cas9 enzyme.

In embodiments the disclosure may further comprise introducing into cells a DNA mutation template that is intended to be fully or partially inserted into a chromosome or other genetic element within a cell via operation of the present improved CRISPR-Cas system. In embodiments the DNA mutation template comprises a DNA sequence that is homologous to a selected locus in a designated chromosome, and thus may be incorporated into a target genetic element via cooperation of the CRISPR system and any type of homologous recombination. In embodiments the DNA mutation template can comprise a DNA segment having any nucleotide length and homology with a host cell genetic segment comprising a selected locus, so long as the length and sequence identity are adequate to introduce the intended genetic change into the locus via functioning of the improved CRISPR-Cas system described herein. In embodiments, the DNA mutation template is a single-stranded oligo DNA nucleotide (ssODN). In embodiments, the DNA mutation template is a double-stranded (ds) template. In embodiments, the DNA mutation template is provided as an episomal element, such as a plasmid or PCR product. The DNA mutation template in certain aspects comprises a segment to be inserted into a chromosome. The segment can be inserted into a protein-coding or non-protein coding portion of a chromosome, or may be present in a regulatory control element, including but not necessarily limited to a promoter or enhancer element, a splice junction, etc.

In embodiments, the mutation template further comprises at least one CRISPR-blocking mutation that is also introduced into the designated chromosome. In embodiments, more than one CRISPR-blocking mutation can be included. A CRISPR-blocking mutation is a mutation that is introduced into the chromosome and functions to prevent CRISPR cutting of the chromosome after the introduction of all or a segment of the repair template, which comprises the blocking mutation. Thus, a CRISPR blocking mutation can, for example, alter or disrupt the PAM site or gRNA binding sequence. In embodiments, the CRISPR blocking mutation is a silent mutation, meaning it does not alter an open reading frame such that an encoded amino acid sequence is changed. In embodiments, the CRISPR blocking mutation introduces a restriction site (or other indicator of the editing event).

In embodiments, the disclosure includes CRISPR systems which target virulent bacteria within a bacteria population, and thus can include targeting RNA directed to bacterial DNA sequences which encode virulence factors, and/or can target antibiotic resistant gene(s). The bacterial population can comprise one type of bacteria, but with virulent and non-virulent members, or the bacterial population can comprise a plurality of bacterial species, with only certain species having virulent and non-virulent members in the population. In embodiments, a mixed bacteria population comprises at least two different strains or species of bacteria. In embodiments, the mixed bacteria population comprises from between two distinct types of bacteria, to up to a thousand distinct types of bacteria. In embodiments, a composition and/or method of this disclosure is adapted for use in a phage-based delivery system and/or to target specific bacteria and/or specific bacterial virulence elements, such as is described in WO/2014/124226, the entire disclosure of which is incorporated herein. In embodiments, the genetic material that is edited using an improved CRISPR-Cas system of this disclosure is or is derived from a segment of a bacteriophage genome.

In embodiments the disclosure includes making modified bacteria that express a Cas enzyme and DNA repair enzyme proteins as described herein for use in a variety of purposes, including but not limited to inhibiting bacteriophage infections, thus providing for enhanced bacterial immunity against phage infections. The method comprises introducing into bacteria a heterologous DNA sequence encoding a Cas enzyme and DNA repair enzyme proteins as described herein, and culturing the bacteria for use in, on or during production of any product, including but not necessarily limited to food and beverage products, and as probiotics, or nutraceuticals. In embodiments, the bacteria are bacteria used in any industrial application, including but not necessarily limited to biofuel production, petroleum spill cleanup, as well as in the production of cosmetics, pharmaceuticals and construction materials. In embodiments, the disclosure comprises modified bacterial cultures themselves. In embodiments, the cultures are propagated as, for example, a yogurt culture. In certain embodiments, the disclosure provides a bacteria starter culture that comprises a Cas enzyme and DNA repair enzymes as described herein and may include progeny of such a starter cultures.

In embodiments, the cells that are modified by the approaches of this disclosure are totipotent, pluripotent, multipotent, or oligopotent stem cells when the modification is made. In embodiments, the cells are neural stem cells. In embodiments, the cells are hematopoietic stem cells. In embodiments, the cells are leukocytes. In embodiments, the leukocytes are of a myeloid or lymphoid lineage. In embodiments, the cells are embryonic stem cells, or adult stem cells. In embodiments, the cells are epidermal stem cells or epithelial stem cells. In embodiments, the cells are differentiated cells when the modification is made. In embodiments, the cells are human, or are non-human animal cells. In embodiments, the cells are mammalian cells. In one approach the cells are engineered to express a detectable or selectable marker or a combination thereof.

In embodiments, the disclosure includes obtaining cells from an individual, modifying the cells ex vivo using an improved CRISPR Cas system as described herein, and reintroducing the cells or their progeny into the individual for prophylaxis and/or therapy of a condition, disease or disorder, or to treat an injury, trauma or anatomical defect. In embodiments, the cells modified ex vivo as described herein are used autologously. In embodiments, the cells are provided as cell lines. In embodiments, the cells are engineered to produce a protein or other compound, and the cells themselves or the protein or compound they produce is used for prophylactic or therapeutic applications.

In various embodiments, the modification introduced into cells according to this disclosure is a homozygous dominant or homozygous recessive or heterozygous dominant or heterozygous recessive mutation correlated with a phenotype or condition, and is thus useful for modeling such phenotype or condition. In embodiments a modification causes a malignant cell to revert to a non-malignant phenotype.

In embodiments, kits for making genetic modifications as described herein are provided. A kit comprises one or more suitable vectors that encode a combination of at least two of CRISPR Cas enzyme, RecBC, AddAB, or AdnAB. The RecBC, AddAB AdnAB that are encoded by the expression vectors may exhibit inactivated nuclease activity. The kits can include plasmids that are suitable for expressing any desirable targeting RNA. The kits can also include other components that are suitable for using the expression vectors to edit DNA in any cell type.

The following examples are presented to illustrate the present disclosure. They are not intended to be limiting in any manner.

EXAMPLES

Figure 1:
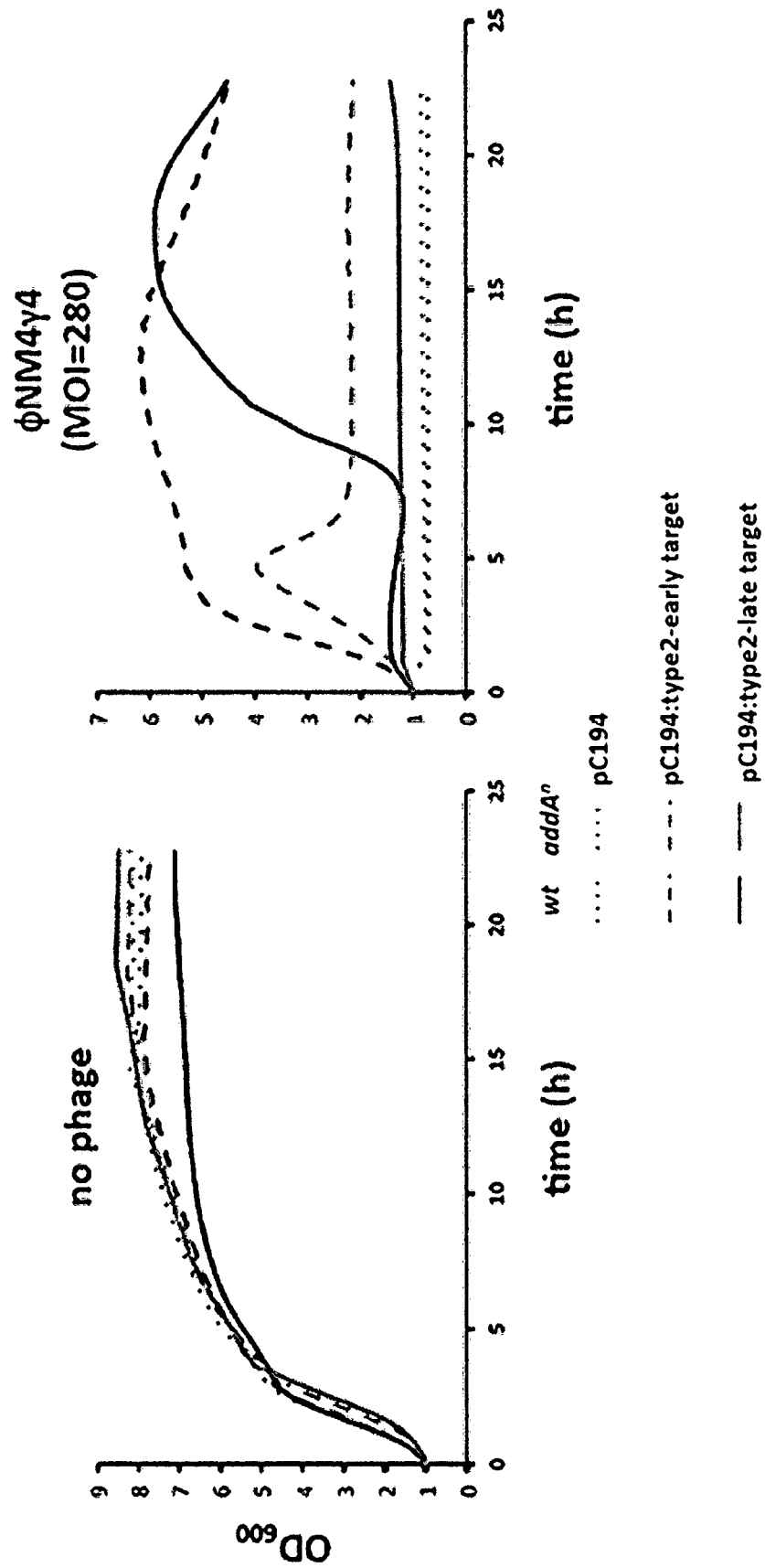

In one non-limiting implementation, it is demonstrated that AddAB enhances Cas9 phage interference in *S. aureus*, as shown in FIG. 1.

Figure 2:
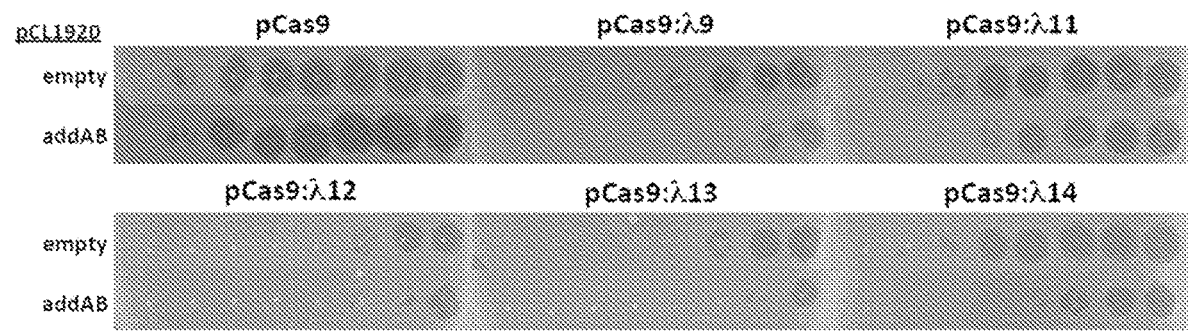

In another non-limiting demonstration, it is shown that SaAddAB (*S. aureus*) enhances Cas9 targeting of phage λ in *E. coli*, as shown in FIG. 2.

Figure 3:
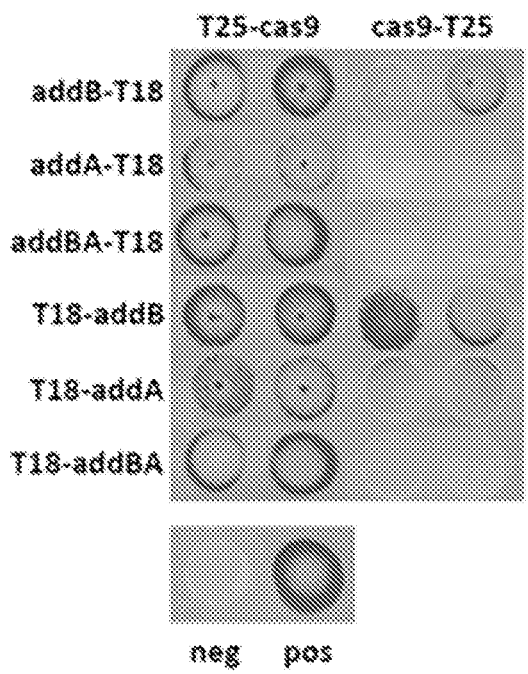

In yet another non-limiting illustration of an embodiment of this disclosure, it is shown that SaAddAB and Cas9 interact in a bacterial two-hybrid system, as depicted in FIG. 3.

In yet another embodiment, in this case in eukaryotic cells, FIG. 4 provides data demonstrating that nuclease-dead RexA and RexB co-expression improves CRISPR/Cas9-mediated HDR in human cells. To obtain the data summarized in FIG. 4, HEK293 cells were transfected with plasmids containing Cas9_2A_GFP, sgRNAs targeting the human APP or PSEN1 gene, repair ssODNs to introduce mutations into APP or PSEN1, and plasmids encoding human codon-optimized RexA and RexB. GFP-positive cells were isolated by fluorescence activated cell sorting (FACS). Cell genomes were analyzed for editing of the APP or PSEN1 locus for HDR or NHEJ. It can be seen from FIG. 4 that HEK293 cells transfected with RexA and RexB show decreased HDR, cells transfected with nuclease-dead versions of RexA and RexB show enhanced HDR, in comparison to cells not transfected with Rex constructs.

It will be recognized from the foregoing results that Cas9 function is compromised in the absence of AddAB, and thus AddAB is necessary for optimum Cas9 cleavage (FIG. 1). Further, if AddAB is expressed recombinantly in *E. coli* (thereby demonstrating insertion of heterologous AddAB because unmodified *E. coli* is not known to express it), Cas9 exhibits enhanced targeting of phage lambda. Thus, the addition of AddAB is sufficient to optimize Cas9 cleavage. Further, a two hybrid analysis of Cas9 interaction with AddAB using modifications of standard two-hybrid approaches demonstrates a physical interaction between the two where the cells turn pink (because the T25 and T18 tags, attached to the N- or C-terminus of each protein interact. Moreover, an embodiment of this disclosure using nuclease-dead RexA and RexB coexpression with Cas9 is shown to function in human eukaryotic cells (HEK293 cells), as shown in FIG. 4 and described in its legend. Analysis of Cas9, RexA and RexB, in the HEK293 cells by immuno-fluorescence-based microscopy shows that RexA and RexB are over 90% co-localized, GFP and Cas9 are over 90% co-localized, and GFP and RexA or B are approximately 70% co-localized.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method comprising:
   providing a cell comprising one or more DNA elements that encode:
   i) a CRISPR-associated Cas9 enzyme;
   ii) a heterologous DNA repair enzyme that is at least one of RecBCD, AddAB, or AdnAB, wherein optionally the RecBCD, AddAB, or AdnAB in the cell has inactivated nuclease activity, and
   iii) a targeting RNA
   wherein the Cas9 enzyme and at least one of the heterologous RecBCD, AddAB, or AdnAB are expressed, and wherein editing of DNA in the cell that is targeted by the targeting RNA occurs.

2. The method of claim 1, wherein the editing of the DNA is enhanced relative to a control value obtained or derived from DNA editing in the absence of the heterologous RecBCD, AddAB, or AdnAB.

3. The method of claim 1, wherein the cell further comprises a DNA repair template, wherein the editing of the DNA in the cell comprises introducing all or a segment of the DNA repair template into the DNA in the cell.

4. The method of claim 3, wherein the DNA repair template comprises at least one mutation that is introduced into the DNA in the cell.

5. The method of claim 4, wherein the mutation comprises a CRISPR-blocking mutation.

6. The method of claim 5, wherein the heterologous RecBCD, AddAB, or AdnAB has the inactivated nuclease activity.

7. The method of claim 6, wherein the cell is a eukaryotic cell.

8. The method of claim 7, wherein the heterologous DNA repair enzyme comprises AddAB or AdnAB.

* * * * *